(12) United States Patent
Bisson et al.

(10) Patent No.: US 6,975,402 B2
(45) Date of Patent: Dec. 13, 2005

(54) TUNABLE LIGHT SOURCE FOR USE IN PHOTOACOUSTIC SPECTROMETERS

(75) Inventors: Scott E. Bisson, Livermore, CA (US); Thomas J. Kulp, Livermore, CA (US); Karla M. Armstrong, Livermore, CA (US)

(73) Assignee: Sandia National Laboratories, Livermore, CA (US)

( * ) Notice: Subject to any disclaimer, the term of this patent is extended or adjusted under 35 U.S.C. 154(b) by 173 days.

(21) Appl. No.: 10/300,421

(22) Filed: Nov. 19, 2002

(65) Prior Publication Data

US 2004/0095579 A1 May 20, 2004

(51) Int. Cl.⁷ .......................................... G01N 21/00
(52) U.S. Cl. .................................................. 356/432
(58) Field of Search ............................... 356/432, 437; 73/579, 655, 24.01, 24.02; 205/492.1

(56) References Cited

U.S. PATENT DOCUMENTS

| | | | |
|---|---|---|---|
| 3,609,389 A | 9/1971 | Bjorkholm ................. 307/88.3 |
| 3,628,186 A | 12/1971 | Rumson et al. .......... 331/107 R |
| 3,948,345 A | 4/1976 | Rosencwaig .................... 181/5 |
| 4,058,725 A * | 11/1977 | Aine ........................... 250/343 |
| 4,457,162 A * | 7/1984 | Rush et al. ................. 73/24.01 |
| 4,622,845 A | 11/1986 | Ryan et al. ..................... 73/24 |
| 5,117,126 A * | 5/1992 | Geiger ....................... 359/330 |
| 5,159,411 A * | 10/1992 | Hammerich et al. ........ 356/432 |
| 5,202,560 A * | 4/1993 | Koch et al. .................. 356/435 |
| 5,434,700 A | 7/1995 | Yoo ............................ 359/332 |
| 5,815,277 A * | 9/1998 | Zare et al. ................... 356/437 |
| 5,903,358 A * | 5/1999 | Zare et al. ................... 356/437 |
| 6,202,470 B1 * | 3/2001 | Chou ......................... 73/24.02 |
| H1965 H | 6/2001 | Burns et al. ................... 372/22 |
| 6,344,647 B1 | 2/2002 | Jourdain et al. ....... 250/339.07 |
| 6,359,914 B1 | 3/2002 | Powers et al. ................. 372/25 |
| 6,618,148 B1 * | 9/2003 | Pilgrim et al. .............. 356/432 |
| 6,757,096 B2 * | 6/2004 | Schiller ....................... 359/330 |
| 6,813,429 B2 * | 11/2004 | Price et al. .................. 385/125 |
| 2002/0017617 A1 * | 2/2002 | Schuth et al. ............. 250/492.1 |
| 2003/0188581 A1 * | 10/2003 | Roudil et al. ................. 73/601 |

FOREIGN PATENT DOCUMENTS

| | | | |
|---|---|---|---|
| EP | 0 857 997 B1 | 10/2001 | ............. G02F 1/39 |

(Continued)

OTHER PUBLICATIONS

J.H. Price et al., "A tuneable, femtosecond pulse source operating in the range 1.06-1.33 microns based on an Yb doped holey fiber amplifier", Apr. 11, 2001, Optoelectronics Research Centre, University of Southhampton.*

(Continued)

Primary Examiner—Layla G. Lauchman
Assistant Examiner—Juan D. Valentin, II
(74) Attorney, Agent, or Firm—Steven R. Vosen

(57) ABSTRACT

The present invention provides a photoacoustic spectrometer that is field portable and capable of speciating complex organic molecules in the gas phase. The spectrometer has a tunable light source that has the ability to resolve the fine structure of these molecules over a large wavelength range. The inventive light source includes an optical parametric oscillator (OPO) having combined fine and coarse tuning. By pumping the OPO with the output from a doped-fiber optical amplifier pumped by a diode seed laser, the inventive spectrometer is able to speciate mixtures having parts per billion of organic compounds, with a light source that has a high efficiency and small size, allowing for portability. In an alternative embodiment, the spectrometer is scanned by controlling the laser wavelength, thus resulting in an even more compact and efficient design.

29 Claims, 13 Drawing Sheets

FOREIGN PATENT DOCUMENTS

WO      WO 98/01927      1/1998      ........... H01S 3/108

OTHER PUBLICATIONS

Gregory David Miller, "Periodically Poled Lithium Niobate: Modeling, Fabrication, and Nonlinear-Optical Performance", Ph.D. Dissertation, Stanford University, Jul. 1998.

L. Goldberg, J. Koplow, D. G. Lancaster, R. F. Curl, and F. K. Tittel, "Mid-infrared difference-frequency generation source pumped by a 1.1-1.5-$\mu$m dual-wavelength fiber amplifier for trace-gas detection", Optics Letters, vol. 23, No. 19, Oct. 1, 1998, pp. 1517-1519.

D. G. Lancaster, D. Richter, R. F. Curl, F. K. Tittel, L. Goldberg, and J. Koplow, "High-power continuous-wave mid-infrared radiation generated by difference frequency mixing of diode-laser-seeded fiber amplifiers and its application to dual-beam spectroscopy", Optics Letters, vol. 24, No. 23, Dec. 1, 1999, pp. 1744-1746.

H. Dahnke, D. Kleine, P. Hering, and M. Mürtz, "Real-time monitoring of ethane in human breath using mid-infrared cavity leak-out spectroscopy", Appl. Phys. B 72, May 9, 2001, pp. 971-975.

Naoya Matsuoka, Shigeru Yamaguchi, Kenzo Nanri, Tomoo Fujioka, Dirk Richter and Frank K. Tittel, "Yb Fiber Laser Pumped Mid-IR Source Based on Difference Frequency Generation and Its Application to Ammonia Detection", Jpn. J. Appl. Phys., vol. 40, Part 1, No. 2A, Feb. 2001, pp. 625-628.

UTA-Barbara Goers, Karla Armstrong, Ricky Sommers, Thomas J. Kulp, Dahv A.V. Kliner, Sal Birtola, Lew Goldberg, Jeffrey P. Koplow, and T.G. McRae, "Development of a compact gas imaging sensor employing a cw fiber-amp-pumped PPLN OPO", Presentation at CLEO, Apr. 2001.

Scott E. Bisson, Karla A. Armstrong, Thomas J. Kulp, and Matthew Hartings, "Broadly tunable, mode-hop-tuned cw optical parametric oscillator based on periodically poled lithium niobate", Applied Optics, vol. 40, No. 33, Nov. 20, 2001, pp. 6049-6055.

CDRL Report No. A009, "Commercialization of Technologies to Lower Defense Costs, Draft Laser-Based Sensors for VOCs, Technology Assessment", 19 pages, Mar. 22, 2002.

"Construction of CW Optical Parametric Oscillators", http//www.nat.vu.nl/vakgroepen/atom/english/research/appspec/opos.html, Aug. 15, 2002.

SERDP Fact Sheet, "Sensors for VOC/NOx and Metal Particulate Emissions Monitoring", Mar. 25, 1999.

* cited by examiner

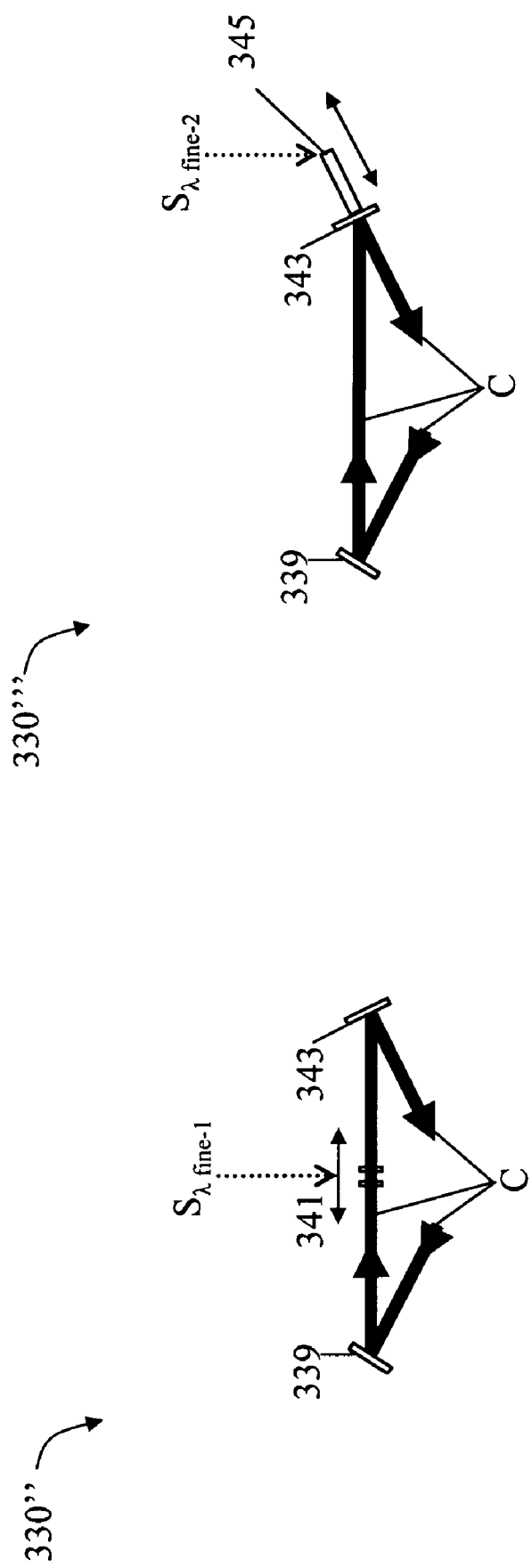

TUNABLE LIGHT SOURCE FOR USE IN PHOTOACOUSTIC SPECTROMETERS

STATEMENT REGARDING FEDERALLY SPONSORED RESEARCH OR DEVELOPMENT

This invention was made with Government support under contract No. DE-AC04-94AL85000 awarded by the U.S. Department of Energy to Sandia Corporation. The Government has certain rights in the invention.

FIELD OF THE INVENTION

The present invention relates to photoacoustic spectrometers and, in particular, to photoacoustic spectrometers having compact, mid-range infrared light sources.

BACKGROUND OF THE INVENTION

The rapid identification of molecular species has many applications in the areas of science and technology. The determination and measurement of harmful pollutants in the environment also has gained increasing importance as government agencies require industries to meet pollution control standards based on the best available testing technologies. The development of inexpensive equipment that can provide a rapid measurement of chemical species in environmental samples can thus have a wide-ranging application.

Various spectroscopic techniques monitor the interaction of laser light with a sample by measuring either transmitted or absorbed laser light as a function of wavelength. Many absorption techniques such as frequency modulation and wavelength modulation spectroscopy estimate species according to the derivative of the spectra. These techniques are best suited to detecting small molecules with well defined spectral features as they are not capable of discriminating the broad spectral features of large molecules. The difference between the spectra of a large molecule, such as toluene, and a small molecule, such as $NO_2$, are illustrated in FIG. 1. In comparison with small molecules, the spectral features of large molecules generally include fine spectral features over a broad spectral range. It is difficult or impossible for many existing laser-based spectroscopic techniques to quantitatively speciate mixtures of such large molecules.

Photoacoustic spectrometers, in contrast to most other techniques, analyze a sample according to heat absorption and the resulting pressure waves generated within the sample. Photoacoustic spectrometers are described, for example, in U.S. Pat. No. 3,948,345 to Rosencwaig, incorporated herein by reference. In photoacoustic spectroscopy, a tunable light source is passed through a sample contained in an enclosed cell. As the wavelength of the light source is varied, the sample absorbs light according to it absorption spectra. Absorbed light is converted into heat within the sample that is detectable as an increase in pressure of the contained sample. The photoacoustic spectrum of the sample is the variation of pressure oscillations in a sample with the wavelength of light from the light source. The ability to speciate mixtures of complex molecules requires a light source having an output that is both tunable over the absorption wavelength range of the molecules and narrow enough to capture fine spectroscopic features of the particular molecules. In addition, sufficient power must be available to produce measurable pressure oscillations or pulses in the sample and distinguish these pulses from background noise. Photoacoustic spectrometers are capable of measuring concentrations of complex molecular species at concentrations of parts per billion, and thus have great potential for the rapid speciation of complex toxic compounds in the air.

Of concern for environmental measurements is the detection of volatile organic compounds (VOCs). The optimum wavelength ranges for detecting VOCs is generally 3–5 $\mu$m and 8–12 $\mu$m, where atmospheric transmission is good and where functional organic groups, such as the fundamental stretch mode of C—H, strongly absorb. At present there are several promising sources in the mid-range infrared range of 3–5 $\mu$m. The most promising sources in the 8–12 $\mu$m range are the $CO_2$ lasers and the quantum cascade diode lasers. The former, however, is only tunable over about 40 discrete lines in the 9 to 11 $\mu$m range. The latter are only tunable over about 10 $cm^{-1}$ per device.

Tunable light in the mid-range infrared can be generated with available light sources through the interaction of laser light with non-linear optical materials. Typically, the output wavelength is varied by changing some physical property of the non-linear material, such as its temperature or orientation. This technique for generating tunable light is particularly promising for environmental uses, since it has the potential to be robust and relatively maintenance-free. Higher output powers and stable output wavelength can be generated non-linear materials by incorporating them into an optical oscillator.

A non-linear material that is particularly useful for spectroscopy and chemical sensing is periodically poled lithium niobate ($LiNbO_3$), or PPLN. U.S. Pat. No. 5,434,700 to Yoo, incorporated herein by reference, describes the operation of optical wavelength converters constructed of materials having non-linear optical properties. The non-linear properties of a PPLN crystal can be changed by changing the material temperature or by adjusting the orientation of light relative to the non-linear material structure, such as by rotating the material relative to the incident light path, or by having a material with varying structures and by moving the material so that different portions of these varying structures intercept the incident light.

While strides have been made in the development of photoacoustic spectrometers, prior art systems have limitations that hinder their use for environmental applications. One of the major limitations is the inability of prior art systems to conduct real-time measurements of mixtures of complex organic compounds. To accomplish this, the light source must be narrow and finely tunable (either continuously, or in steps of a fraction of a wave number) over a broad range (hundreds of wavenumbers). In addition, it must be capable of being used at the place where the environmental measurement is to be made that is it must be portable so that is useful in the field.

Prior art systems typically use lasers having an output in the several watt range to drive non-linear materials. For example, such systems have used neodymium-vanadate (Nd:Vanadate) pump lasers operating at about 1 $\mu$m and generating sufficient power to induce non-linear effects in non-linear materials, such as PPLN. Typically the non-linear material in located in an optical parametric oscillator (OPO) that is tuned to produce light of a wavelength different from the pump laser. While these systems produce usable IR light, there are many problems in adapting them for portable applications, such as real-time environmental measurements. Prior art systems typically have limited tuning capabilities and require large amounts of external power, making it difficult to include them in portable photoacoustic spectrometers.

What is needed is an improved photoacoustic spectrometer which has a laser system that operates at high efficiency and generates light with a beam profile that efficiently couples into an OPO, which is be capable of speciating gaseous mixtures of complex organic molecules, and which is robust and portable.

SUMMARY OF THE INVENTION

The present invention solves the above-identified problems with photoacoustic spectrometers by providing a compact and efficient solid state laser system to drive a PPLN crystal in an OPO.

It is one aspect of the present invention to provide photoacoustic spectrometers that is portable and rugged for use in the field.

It is another aspect of the present invention to provide a photoacoustic spectrometer that can speciate mixtures of volatile organic compounds.

It is one aspect of the present invention to provide a photoacoustic spectrometer for analyzing a sample including a light source, a photoacoustic cell, and a controller, where the light source has a laser and an OPO for generating a beam of an adjustable wavelength light from the laser. The OPO has a light path and a material with non-linear optical properties within the light path, a first tuner to vary the adjustable wavelength by modifying said non-linear optical properties within the light path, and a second tuner to vary said adjustable wavelength by modifying the oscillating frequency of the OPO. The photoacoustic cell is adapted to contain the sample and has at least one window to accept the generated beam and irradiate a sample, and a pressure transducer adapted to provide an indication of the pressure of the sample; and a controller to scan said adjustable wavelength. In one embodiment, the non-linear material is a PPLN crystal.

It is another aspect of the present invention to provide a photoacoustic spectrometer that has a light source that includes an Yb-fiber pumped OPO having a PPLN crystal, where the OPO is finely tuned by continuous or mode-hopped tuning of the OPO cavity and is coarsely tuned by moving a fan-shaped PPLN crystal in the optical cavity of the OPO.

It is yet another aspect of the present invention to provide a photoacoustic spectrometer for analyzing a sample including a light source, a photoacoustic cell, and a controller, where the light source has a laser system including a laser and an optical-fiber amplifier adapted to amplify light from said laser, and an OPO having a non-linear optical material for generating a beam of an adjustable wavelength light from said amplified laser. The photoacoustic cell is adapted to contain the sample and has at least one window to accept the generated beam and irradiate a sample, and a pressure transducer adapted to provide an indication of the pressure of the sample; and a controller to scan said adjustable wavelength.

It is an aspect of the present invention to provide a photoacoustic spectrometer that has a light source that includes a neodymium-yttrium aluminum garnet (Nd:YAG) laser, amplified by a Yb-fiber amplifier, to drive an OPO having a PPLN crystal, where the OPO is finely tuned by continuous or mode-hopped tuning of the OPO cavity and is coarsely tuned by moving a fan-shaped PPLN crystal in the OPO cavity.

It is yet another aspect of the present invention to provide a photoacoustic spectrometer for analyzing a sample including a light source, a photoacoustic cell, and a controller, where the light source has a laser system with a laser having a wavelength adjustable output that is adjustable within the range from approximately 750 to approximately 900 nm. The amplifier output is provided to an OPO for generating a beam of an adjustable wavelength light from the amplified laser, which has a fixed light path and a fixed non-linear material. The spectrometer also includes a photoacoustic cell to contain a sample and has at least one window to accept said generated beam and irradiate a sample, and a pressure transducer adapted to provide an indication of the pressure of the sample. A controller is provided to control the wavelength of the pump laser.

A further understanding of the invention can be had from the detailed discussion of the specific embodiment below. For purposes of clarity, this discussion refers to devices, methods, and concepts in terms of specific examples. However, the method of the present invention may be used to connect a wide variety of types of devices. It is therefore intended that the invention not be limited by the discussion of specific embodiments.

Additional objects, advantages, aspects and features of the present invention will become apparent from the description of preferred embodiment set forth below.

BRIEF DESCRIPTION OF THE DRAWING

The foregoing aspects and the attendant advantages of the present invention will become more readily appreciated by reference to the following detailed description, when taken in conjunction with the accompanying drawings, wherein:

FIGS. 4A–C are optical layouts of OPO embodiments, where FIG. 4A is an optical layout of a preferred OPO embodiment having one coarse tuning mechanism that uses a non-linear material and two fine tuning mechanisms, one that uses an etalon and one that translates a mirror of the OPO cavity; FIG. 4B is an optical layout of another preferred OPO embodiment having one coarse tuning mechanism that uses a non-linear material and one fine tuning mechanisms that uses an etalon; and FIG. 4C is an optical layout of another embodiment having one course tuning mechanism that uses a non-linear material and one fine tuning mechanisms that translates a mirror of the OPO cavity;

Reference symbols are used in the Figures to indicate certain components, aspects or features shown therein, with reference symbols common to more than one Figure indicating like components, aspects or features shown therein.

DETAILED DESCRIPTION OF THE INVENTION

The present invention will now be described with reference to the Figures. The description that follows will first describe several embodiments of the photoacoustic spectrometer of the present invention, and is followed with detailed descriptions of the OPO and of the tuning of the OPO. A description of cell calibration and data acquisition are then presented, followed by alternative embodiments.

Figure 1:
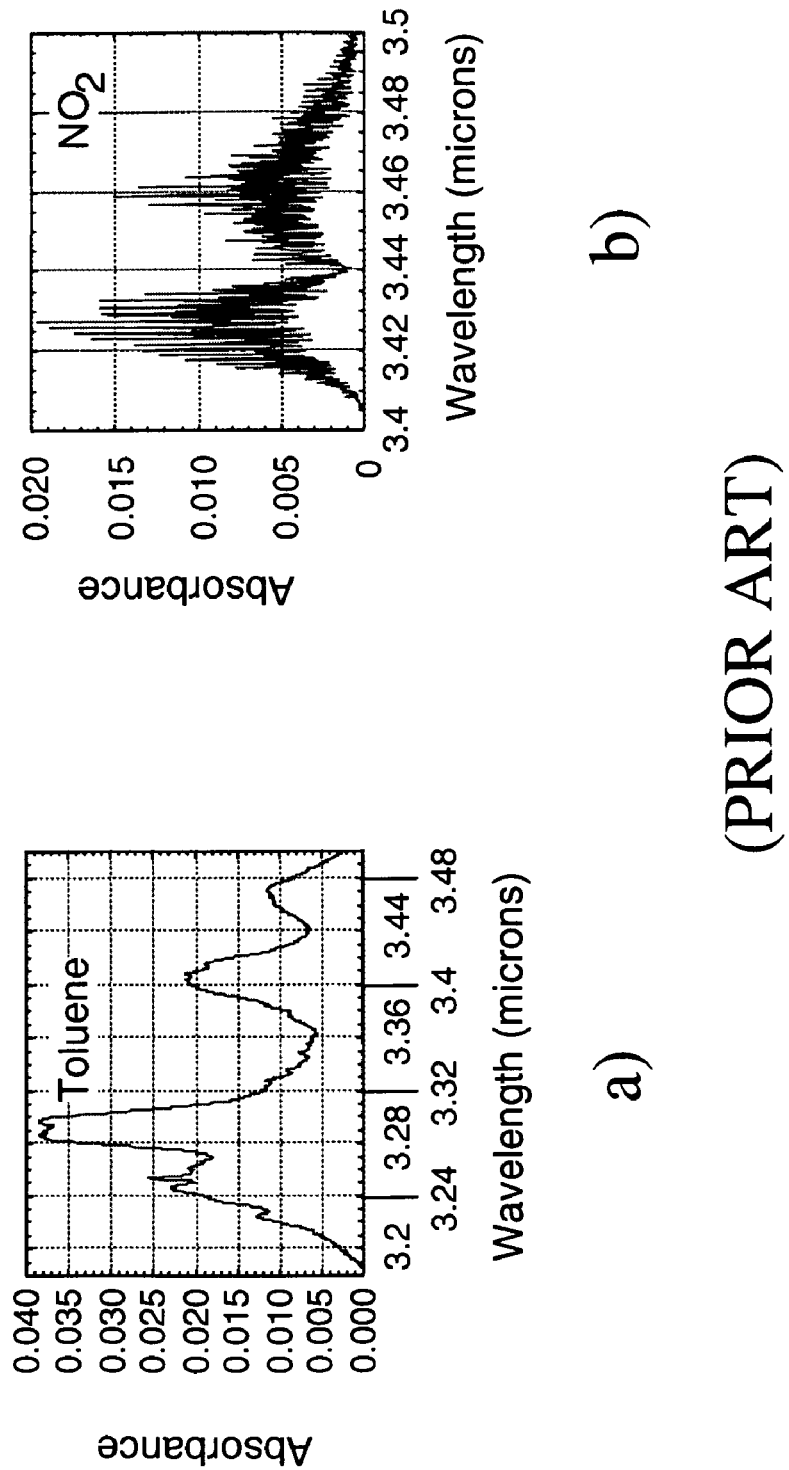
FIG. 1 is a comparison of the absorption spectra for (a) toluene (a large molecule) and (b) $NO_2$ (a small molecule)
Figure 2:
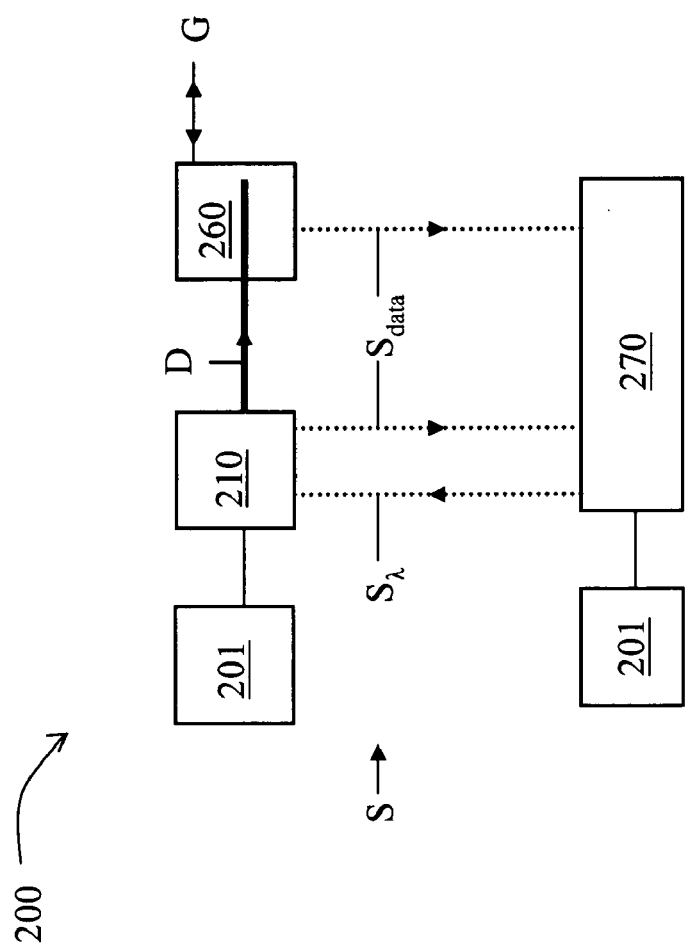
FIG. 2 is a schematic of an embodiment of the photoacoustic spectrometer of the present invention.

FIG. 2 is a schematic of an embodiment of a photoacoustic spectrometer 200 of the present invention. Photoacoustic spectrometer 200 includes a tunable light source 210, a photoacoustic cell 260 adapted for receiving a gas sample and accepting light from the light source, and a control and data acquisition system 270. The gas sample is admitted into cell 260 from a source G that can be from the environment or from a sampling container, and can be admitted either continuously or as a fixed volume. Cell 260 has windows (not shown) that allow for the transmission of light beam D into the gas sample and a pressure transducer or microphone (not shown) to monitor variations in the pressure P of the sample.

Light source 210 produces a beam D of light having a narrow spectral distribution about a tunable wavelength $\lambda_D$, and provides the light to the sample within cell 260 with intensity I. Wavelength $\lambda_D$ of beam D is adjustable and, preferably, is capable of being modulated so that the intensity I of beam D may be pulsed. In one embodiment, the inventive spectrometer provides for fine tuning of light source 210, with steps of less than 0.1 cm$^{-1}$ over a broad spectral range of from approximately 100 cm$^{-1}$ to approximately 300 cm$^{-1}$ or more.

System 270 sends control signals $S_\lambda$ and receives signals $S_{data}$ from light source 210 and cell 260 to control light source 210, and obtain data from the light source and cell 260. Specifically, system 270 controls, through signal $S_\lambda$, the wavelength $\lambda_D$, and receives information regarding the intensity I and pressure P as signals $S_{data}$. System 270 can include a computer having appropriate interfaces for sending and receiving signals as well as specialized data acquisition components, such as lock-in amplifiers, and controllers, such a stepper motor controllers for adjusting experimental parameters such as laser wavelength, power or control gas into out of cell 260, and data analysis and display devices.

Unlike prior art photoacoustic spectrometers, photoacoustic spectrometer 200 is small, efficient, and has a low power consumption rate. As such, spectrometer 200 can be provided in a self-contained package that is portable and rugged enough for field use. Spectrometer 200 thus also includes one or more batteries 201 to power the spectrometer, including but not limited to light source 210 and system 270.

The photoacoustic spectrum of a sample is determined by measuring pressure waves in a contained sample as a function of the wavelength of absorbing light as follows. Absorption of light of wavelength $\lambda_D$ by the gas in cell 260 both locally and nearly instantaneously raises the temperature of the absorbing gas, and is quickly converted into a localized pressure increase. When beam D is pulsed, the absorption of light results is thus converted into localized pressure pulses in the gas. As the wavelength $\lambda_D$ is varied, pressure pulses are generated that have an amplitude that varies with the absorption coefficient of the sample.

In general, photoacoustic cell 260 has the following characteristics that result in a spectrometer that is well-suited for use in the field. The size of spectrometer 200 is decreased and the sensitivity in increased by amplifying the laser-induced pressure oscillations. Acoustic amplification of laser-induced pressure oscillations are provided by having a photoacoustic cell that is acoustically resonant at a modulation frequency of the laser, and that allows access of the laser to regions in the cell where the pressure oscillations are greatest. In some instances there is an interaction of the laser light with the photoacoustic cell windows through which it passes. Acoustic disturbances from this interaction are reduced by isolating the resonant chamber from the windows with a cell cavity enlargement near the windows. A large photoacoustic cell mass is also desirable to dampen external acoustic noise. Also, rapid analysis of samples is facilitated by having a photoacoustic cell volume that is small, permitting rapid exchange of the gas volume.

Acoustic amplification of the pressure oscillations in photoacoustic cell 260 results from the interaction of beam D and the gas contained within cell 260. The gas contained in cell 260 has numerous acoustic modes at which it can resonate. These acoustic modes are determined by shape standing acoustic waves in the volume of gas in cell 260. For example, a cylindrical volume of finite length can support an infinite number of discrete modes combining pressure distributions in the shape of radially dependent Bessel's functions and longitudinal sine or cosine waves. The lowest radial and longitudinal frequency modes have periodic pressure waves whose amplitude varies monotonically from the center to the edge of the cylinder. The acoustic oscillation frequency of the individual modes is proportional to the speed of sound of the gas in cell 260. The sound speed is a thermodynamic property of the gas that depends on the gas constituents, pressure and temperature.

When the pulsing of beam D occurs at the frequency of an acoustic mode of the gas in cell 260, and when the absorbed energy is deposited in time with the oscillations such that energy is locally deposited near pressure maximums, the energy of the absorbed light is then acoustically coupled to the resonating gas, amplifying the pressure waves. This amplification of pressure waves through this process is analogous to the timed pushing of a pendulum, where the pushes are timed to the oscillation of the pendulum and the energy input occurs when the potential energy is greatest.

The proper timing of the position and pulsation frequency of beam D thus increases the pressure oscillations for a given amount of light absorption, effectively increasing the sensitivity of the spectrometer. Acoustic amplification by a factor, Q, of greater than 100 is possible, increasing the sensitivity of the photoacoustic spectrometer. Acoustic amplification is exploited by varying the intensity I between a high value and low value, preferably zero. Measurements of P and $\lambda_D$ can then be used by processor 270, or are transmitted to another system to determine the photoacoustic spectra, $P(\lambda_D)$. It is known that the pressure P increases linearly with the intensity I, and thus the intensity I can be used to normalize by the pressure P to obtain intensity independent spectra, $P'(\lambda_D) = P(\lambda_D)/I(\lambda_D)$.

Figure 3:
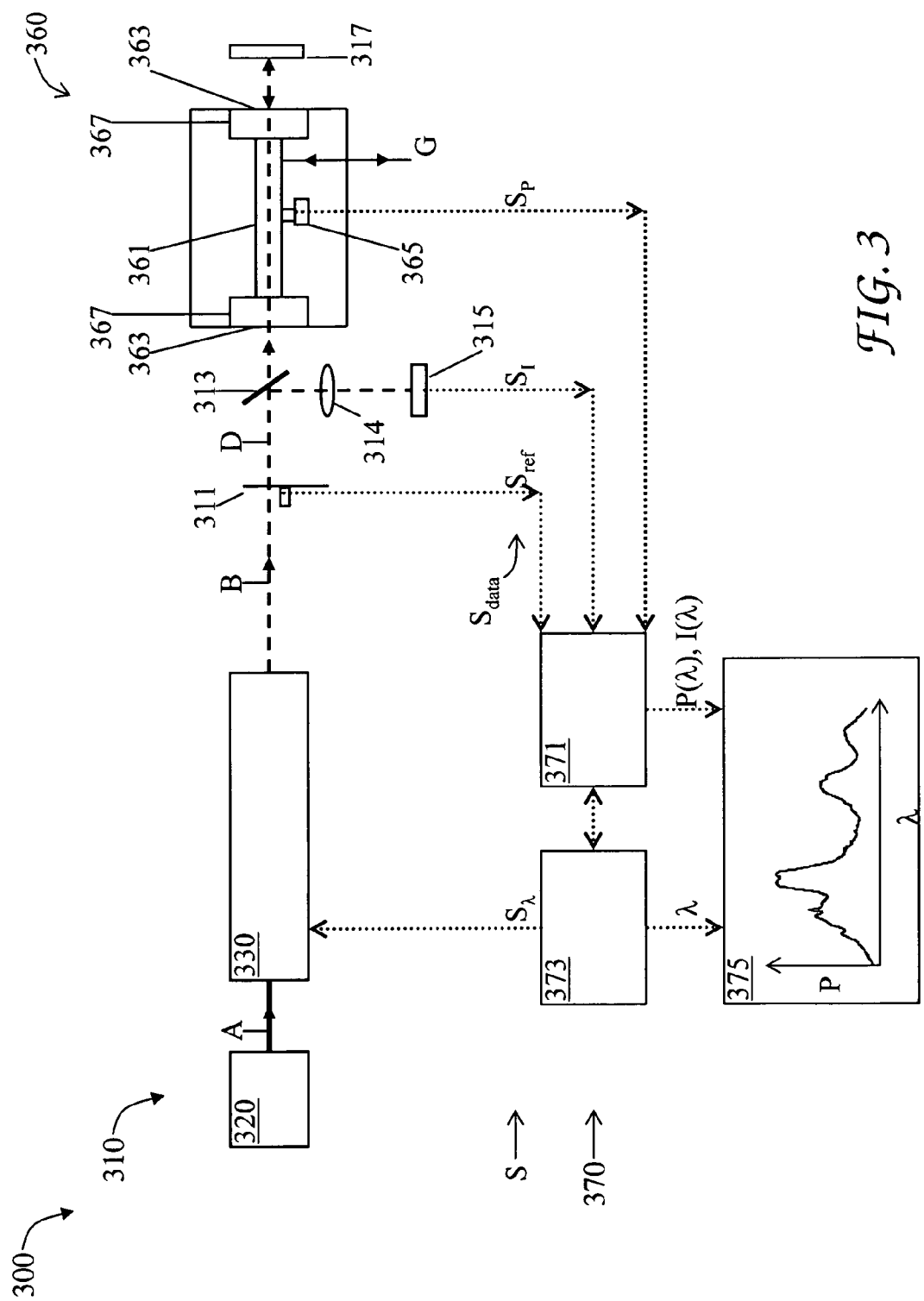
FIG. 3 is an optical layout of a preferred embodiment photoacoustic spectrometer of the present invention.

FIG. 3 shows a preferred embodiment of a photoacoustic spectrometer 300. Photoacoustic spectrometer 300 includes a tunable light source 310 that is capable of generating a periodically modulated light beam D of adjustable wavelength to probe a sample of gas G in a photoacoustic cell 360. Spectrometer 300 also includes a control and data acquisition system 370 that controls and/or monitors light source 310 and acquires a photoacoustic spectrum of sample G.

Light source 310 has optical and mechanical elements that cooperatively adjust the wavelength $\lambda_D$ of light beam D and provides light beam D to cell 360. Specifically, light source 310 includes a laser system 320, an OPO 330, a modulator 311, and a reflector 317. Light source 310 also includes a beam splitter 313, a lens 314, and a light detector 315 that are used maintain the intensity of beam D.

Figure 6:
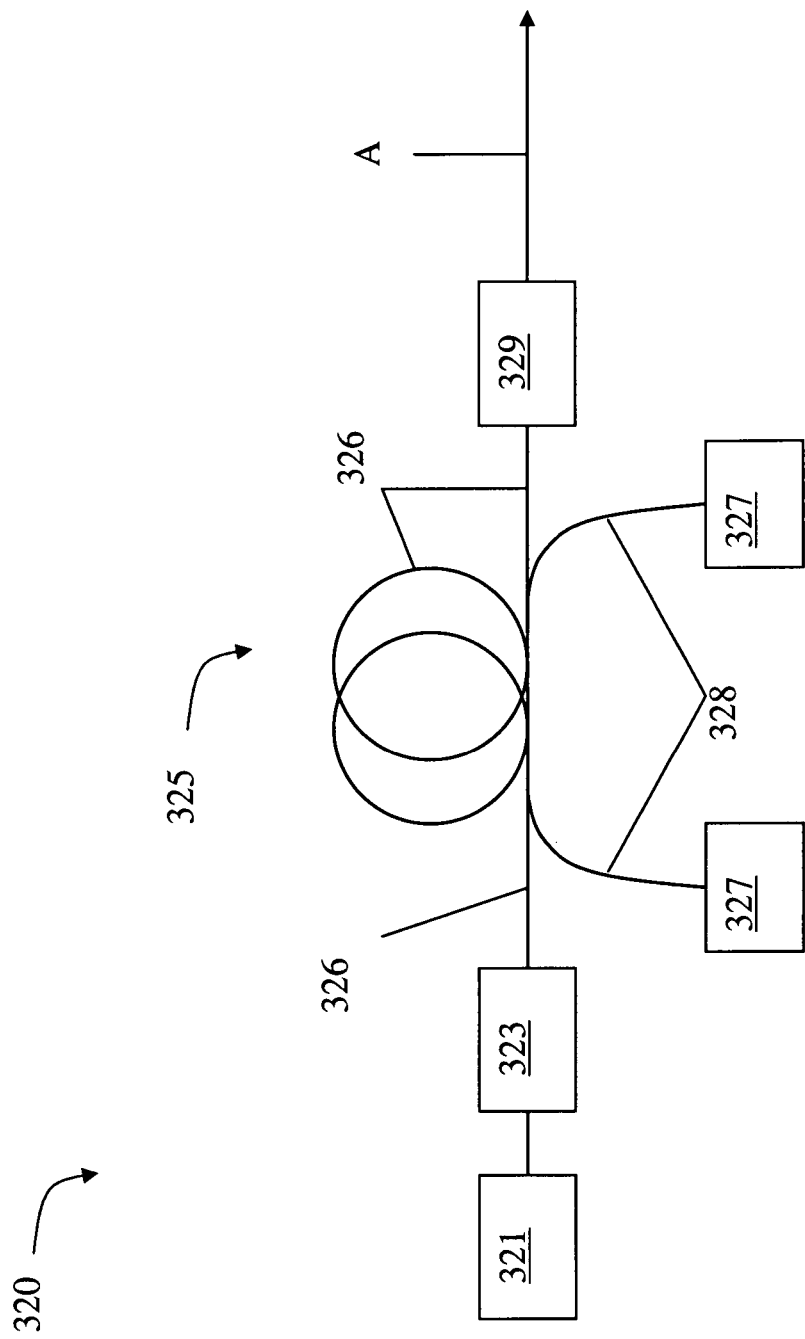
FIG. 6 is a schematic diagram of the doped-fiber amplifier of the preferred embodiment.

As shown in FIG. 6, laser system 320 includes a laser 321, a Faraday isolator 323, an optical-fiber amplifier 325, and a fiber port 329. In one embodiment, laser 321 is a cw diode seed laser, such as an Nd-based laser, having a narrow spectral output in the mid-IR of several to a few hundred milliwatts and a linewidth of less than about 100 MHz.

Light from laser 321 is amplified by optical-fiber amplifier (OFA) 325 which includes a doped fiber 326, and one or more pump lasers 327 that are each coupled to fiber 326 through coupling fibers 328. Faraday isolator 323 is provided between laser 321 and optical-fiber amplifier 325 to isolate the laser from upstream reflections. OFA 325 is similar to doped fiber amplifiers that are known and used in the telecommunications industry, such as an erbium-doped fiber amplifier. It is preferred that fiber 326 is an Ytterbium (Yb) doped fiber, as this type of fiber amplifier is well-suited to amplifying light at 1.06 μm. Pump laser 327 supplies light at 980 nm and is mixed with the output of laser 321, causing the incident light at 1.06 μm to be amplified within fiber 326. The amplified laser output in fiber 326 passes from OFA 325 through fiber port 329 as beam A with sufficient power for use by OPO 330 to generate beam B. In a preferred embodiment, laser 321 is an Nd:YAG laser that is amplified by Yb-doped OFA 325 to a power of from 4 to 6 watts at $\lambda_A$=1.06 μm. In a particularly preferred embodiment, laser 321 has a power of about 50 to about 100 milliwatts.

OPO 330 includes one or more non-linear elements that accept light of one wavelength (beam A of wavelength $\lambda_A$) and can tunably generate light of two different wavelengths. In general, optical parametric oscillators operate more stably in a continuous mode and at a single wavelength, and thus it is preferred that laser 321 is a continuous wave (cw) laser that oscillates in a single-longitudinal-mode (SLM), and that OPO 330 be singly resonant.

The selection of a laser 321 and an OFA 325 is governed by the necessity to efficiently generate a pump beam A that is both spectrally narrow and has sufficient power to induce non-linear light generation in OPO 330 at low cost. The specifications on wavelength and power are to be understood in conjunction with the operation of the OPO. Since the amount of power required to generate beam B will depend on wavelength $\lambda_A$, different combinations of lasers and amplifiers are within the scope of the present invention. For example, optical-fiber amplifiers contain different dopants depending on wavelength $\lambda_A$, and the amount of power required to drive the non-linear material of the OPO decreases with decreasing wavelength $\lambda_A$. For example, 1.55 μm light is best amplified with an erbium-doped fiber amplifier, but such systems require higher powers to operate an OPO.

The combination of laser 321 and OFA 325 thus has several features that make it advantageous for use in photoacoustic spectrometers and particularly advantageous for use in a field portable photoacoustic spectrometer. First, the amount of power required to operate preferred laser system 320 is much less than that required for operating an Nd:Vanadate laser having similar output characteristics. An Nd:Vanadate laser having 6 W of output power at 1.06 consumes only approximately 60 W of electrical power. The reduced power consumption allows for use of battery power for the various lasers, as well as the data acquisition and control system and ancillary electronics. Further, the preferred laser system is much less expensive than prior art systems. For example, currently the cost of a 6 W Nd:Vanadate laser is $70,000, while the combined Nd:YAG/Yb-doped fiber amplifier having 6 W of output power costs $20,000. Third, the inventive system is easily tunable. This allows for tuning the wavelength of the light source through tuning of laser 321, or OPO 330, or a combination thereof. Laser tuning allows use of more advanced techniques for acquiring photoacoustic spectra, such as by dithering the excitation frequency to provide differencing measurements.

After exiting OPO 330, beam B is periodically interrupted by modulator 311 to produce periodic beam D at a wavelength $\lambda_D$ that is the same wavelength as beam B ($\lambda_D=\lambda_B$). Modulator 311 also generates a data signal $S_{ref}$ that provides a chopping frequency reference that is useful for data analysis. In one embodiment, modulator 311 includes a rotating disk that periodically allows beam B to pass through, thus generating a periodic beam D according to the rotation rate of the disk and the pattern of openings on the disk. Alternatively, modulator 311 could be a rotating prism or a solid state device, such as an acousto-optic modulator.

The intensity of beam D is monitored by extracting a small portion of the beam with beam splitter 313, though lens 314, to light detector 315. It is preferable that beam D is monitored by sampling a small portion of the beam, such as 1–5% of the incident beam. Lens 314 tightly focuses the sampled light onto the face of detector 315, which responds to the temporal variation of the intensity I of beam D by generating a data signal $S_I$. Infrared detectors, such as detector 315 are well known in the art. It is preferred that detector 315 has a flat spectral response over the spectral range of beam D and that there are no windows to cause etaloning of the sampled beam. A preferred brand of detector is a pyrometer manufactured by Molectron Detector, Inc. (7470 SW Bridgeport Road, Portland, Oreg. 97224) with a detector area of approximately 5 mm².

The portion of beam D that passes undeflected by beam splitter 313 continues onto cell 360 and is reflected back towards the cell by reflector 317, resulting in a double-pass through the sample gas.

Photoacoustic cell 360 accepts a sample G and has a pressure transducer 365 that produces a pressure-level proportional signal $S_P$. In one embodiment, transducer 365 is a hearing aid microphone. The pressure levels generated in cell 360 when determining the photoacoustic spectra are typically acoustic waves at a frequency on the order of about 1 kHz. The measurement of acoustic pressures is well known in the art, and there are many pressure transducers that are capable of accurately measuring these pressures.

Signal $S_P$, which is indicative of the pressure of the sample in cell 360 depends on a number of factors: the overlap of the laser beam and those areas of the acoustic mode having large pressure oscillations, the intensity of the laser beam, the excitation or chopping frequency, the volume and acoustic amplification, Q, of the cell and the absorption properties of the gas. While a large Q would appear to be desirable, it was found that such a cell is also prone to picking up background noise and is sensitive to environmental factors, such as changes in temperature. After testing several cells, it was found that a cell with a Q of about 10 produced good photoacoustic sensitivity and low noise. As an example of such a cell is shown schematically in FIG. 3. Specifically, cell 360 has a cylindrical volume 361, a pair of acoustic filters 367 at the cylinder ends, and a window 363 near each filter. Windows 363 are transparent to beam D, and can be manufactured, for example, from ZnSe tilted at Brewster's angle to reduce reflection losses and to avoid stray reflections which could raise the acoustic background level.

One cylindrical volume 361 that was found to produce good results when illuminated by the Coherent light source has a length of 15 cm and a diameter of 9 mm, resulting in a lowest acoustic resonance frequency corresponding to the first longitudinal acoustic mode. This volume has an oscillation frequency, when filled with an atmospheric sample, of approximately 1,600 Hz. The small volume allows for quick gas exchange and thus quick data acquisition. Acoustic filters 367 are enlarged cavity volumes that acoustically dampen noise generated by absorption of the laser beam at the surface of the windows from reaching transducer 365. Cell 360 has a lowest frequency mode with pressure waves that vary sinusoidal in time and that have a peak pressure along the cylinder centerline. Acoustic coupling of light absorption of a wavelength $\lambda_D$ into a cylindrical sample can thus be accomplished by pulsing beam D along the cylinder centerline at a frequency corresponding to that acoustic mode.

Windows 363 and volume 361 are aligned with beam D, including reflector 317, to provide a double pass of beam D through cell 360. Since only a small portion of beam D is absorbed by the sample in cell 360, the amount of energy absorbed by the sample, and thus the pressure P, increases with the number of passes of light through the cell. However, it has been found that each pass through cell 360 also increases the noise in signal $S_p$ due to scattering at the windows. For configurations with more than two passes, an off-axis beam geometry is required that makes is more difficult to aim the beam through the cell. The effects, coupled with beam profile changes that were observed with etalon mode hops, produced a noticeable modulation in the photoacoustic signal when more than two passes were used. Although filters 367 reduce the amount of noise, it is preferred that a two-pass configuration be used to increase the signal $S_p$ without unduly increasing the complexity of the cell or increase noise in the system.

Figure 8:
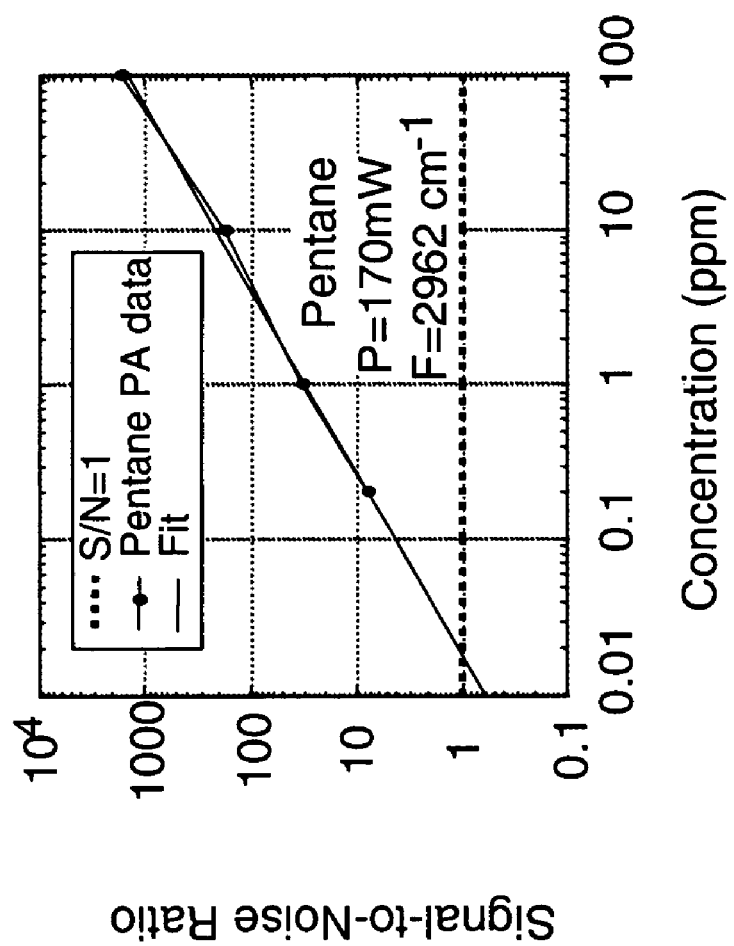
FIG. 8 is a graph showing the sensitivity of the preferred embodiment photoacoustic spectroscopy cell for ethane and pentane using an unamplified, 6 W, SLM, 1.06 $\mu$m Nd:Vanadate laser manufactured by Coherent Inc (5100 Patrick Henry Drive, Santa Clara, Calif. 95054)(the "Coherent light source")

The sensitivity of cell 360 as determined for ethane and pentane using the Coherent light source is shown in FIG. 8. The measurements shown in FIG. 8 were made with the sample gas diluted in pure nitrogen and at atmospheric pressure, and indicate extrapolated sensitivities of approximately 15 ppb for ethane, and approximately 22 ppb for pentane. Cell 360 is thus seen to have the sensitivity required to detect small quantities of organic compounds.

System 370 preferably includes processor 373, an amplifier 371 that is preferably a lock-in amplifier, and a display unit 375. Processor 373 controls the adjustment of wavelength $\lambda_B$. Amplifier 371 receives reference signal $S_{ref}$, intensity signal $S_I$, and pressure signal $S_P$, and effectively amplifies those components of the intensity and pressure having a component occurring at the chopping frequency. In one embodiment, amplifier 371 includes two separate lock-in amplifiers, one amplifier which accepts reference signal $S_{ref}$ and intensity signal $S_I$, and the other amplifier accepts reference signal $S_{ref}$ and pressure signal $S_P$.

Display unit 375 receives wavelength, pressure and intensity information that is used to generate a visual display of the photoacoustic spectra. Preferably, amplifier 371 provides a normalized pressure output to display unit 375, such as the ratio of the pressure to intensity.

Optical Parametric Oscillator

Figure 4A:
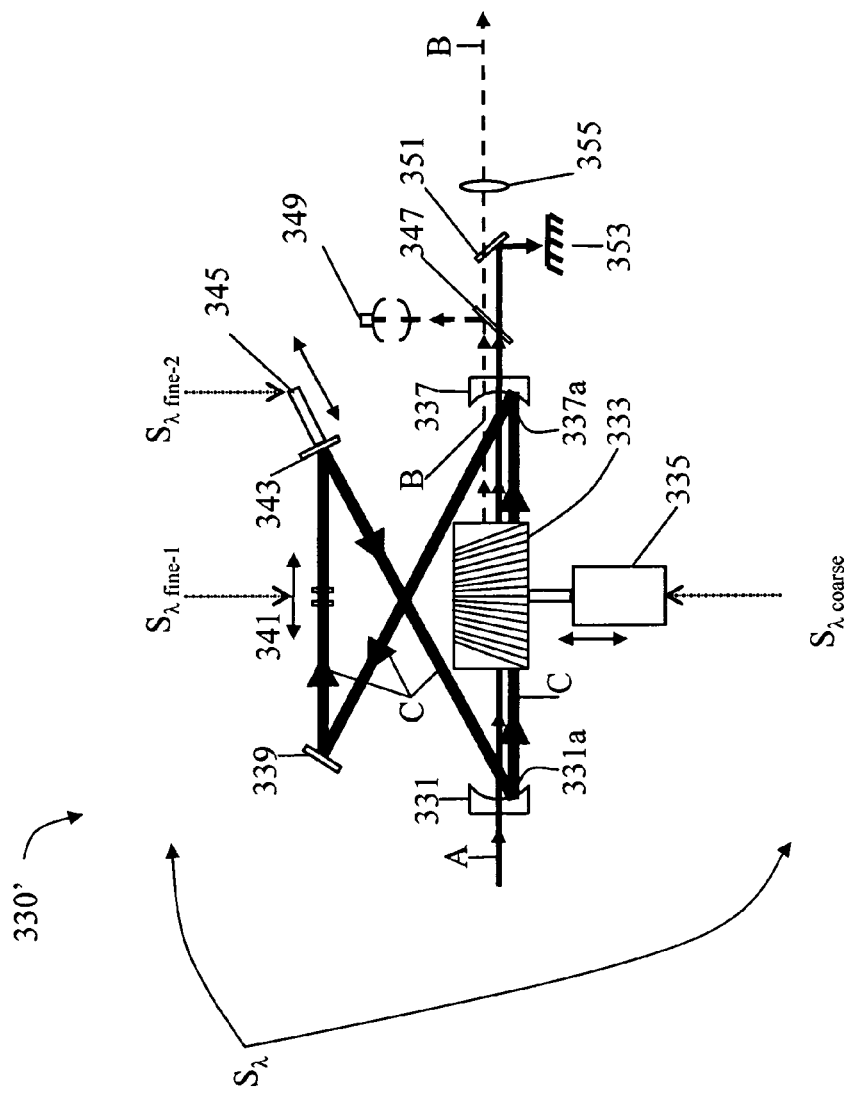

FIGS. 4A–C are optical layouts three preferred embodiments of OPO 330, shown an OPO 330', and OPO 330", and an OPO 330''', respectively. The embodiments of FIG. 4 differ according by their fine tuning mechanisms. FIG. 4A is an optical layout of a preferred embodiment of OPO 330' having one coarse tuning mechanism that uses a non-linear material and two fine tuning mechanisms as described below, one that uses an etalon and one that translates a mirror of the OPO cavity. FIGS. 4B and 4C each have the same general optical layout as OPO 330', but each has only one of the fine tuning mechanisms of OPO 330'. Specifically, FIG. 4B is an optical layout showing the fine tuning portion of OPO 330" that uses an etalon; and FIG. 4C is an optical layout showing the fine tuning portion of OPO 330''' that translates a mirror of the OPO cavity. The following discussion of FIG. 4A thus applies to the embodiments of FIGS. 4B and 4C with respect to their respective tuning mechanism.

FIG. 4A shows a schematic of a preferred embodiment an OPO system 330', which accepts beam A from laser system 320, oscillates a beam C, and provides an output beam B. OPO 330 includes a pair of plano-concave mirrors 331 and 337, a pair of planar mirrors 339 and 343, a non-linear optical material 333, an intra-cavity etalon 341, a first beam splitter 347, a diagnostic etalon 349, a second beam splitter 351, a beam dump 353, and a lens 355.

Mirrors 331, 337, 339, and 343 form an optical cavity, as shown by the path of beam C. Beams A and B pass out of the optical cavity through mirror 337. Preferably, a small portion of beam B is sampled by beam splitter 347 to diagnostic etalon 349 to monitor the wavelength of beam A, and the remaining beam A is separated by beam splitter 351 into beam dump 353, allowing beam B to exit OPO 330 after being collimated by lens 355. OPO 330 also includes a coarse tuning mechanism and at least one fine tuning mechanism, described subsequently.

As described subsequently, non-linear optical material 333 interacts with a beam A to generate a beam B and a beam C. Specifically, non-linear material 333 within the path of beam A generates two coaxial beams: a beam B having a wavelength $\lambda_A$ and beam C. (These beams are shown schematically in FIG. 3 as being laterally displaced.) Beams A, B, and C are reflected and/or transmitted by planar mirrors 339 and 343 and mirrors 331 and 337, along with concave surfaces 331a and 337a of respectively, as follows. Mirrors 331 and 337 have high transmissivities for the wavelength range of beam A, allowing beam A to substantially pass once through OPO 330. Mirror 337 also has a high transmissivity for the wavelength range of beam B, allowing beam B to substantially exit OPO 330 after being generated by non-linear optical material 333. Planar mirrors 339 and 343 and mirrors 331 and 337 are highly reflectivity at the wavelength range of beam C. The high reflectivity of mirrors 339, 343, 331, and 337 and the curvature of concave surfaces 331a and 337a allow a substantial portion of beam C to recirculate through OPO 330, in a "bow-tie" configuration, and in particular to make multiple passes through non-linear optical material 333.

The "bow-tie" configuration of OPO 330 provides better frequency stability, single mode operation and more space for intra-cavity tuning elements than other configurations. Specifically, the geometry of OPO 330 supports single mode or single frequency operation, without intra-cavity tuning elements. This is not the case with linear resonators, which suffer from random mode hopping and multi-mode operation.

In one embodiment of OPO 330, curved surfaces 331a and 337a have a radius of curvature of 10 cm with non-linear optical material 333 centered between mirrors 331 and 337 and mirrors 339 and 343. An example of acceptable coatings for beam A wavelength of 1.064 µm, beam B wavelength of 3.3 µm, and beam C wavelength of 1.57 µm is as follows. Mirrors 331 and 337 are coated on both sides for high transmission (>98%) of the beam A at 1.064 µm and for high reflectivity (>99.5%) on the curved surfaces for beam C at 1.57 µm. The reflectivity of mirror 337 at the wavelength range of beam B (3.3 µm) is as low as possible (<10% for curved surfaces 331a and 337a and <0.1% for planar mirrors 339 and 343) to couple as much 3.3 µm light out of the cavity of OPO 330 as possible and to avoid feedback from beam C, since feedback of $10^{-4}$ or greater per roundtrip can result in double resonance. OPO 330 thus supports resonating beam C and allows beams A and B to pass through mirror 337.

Since the spectra of beam B is a function of the spectra of beam A, it is preferable to operate laser 321 in a single-longitudinal-mode to achieve single frequency operation of OPO 330. In general, a multi-mode laser 321 could be used if the idler wave (beam B) were resonated inside the OPO cavity instead of the signal wave (beam C). However, this is difficult due to mirror coating considerations. Beam A is focused to approximately 100 µm in intensity diameter inside the PPLN crystal. The oscillation threshold of OPO 330 operated as a cw, singly resonant OPO is approximately 3 watts and when pumped at 6.5 watts, the OPO depletes beam A by 85–90%.

Figure 5:
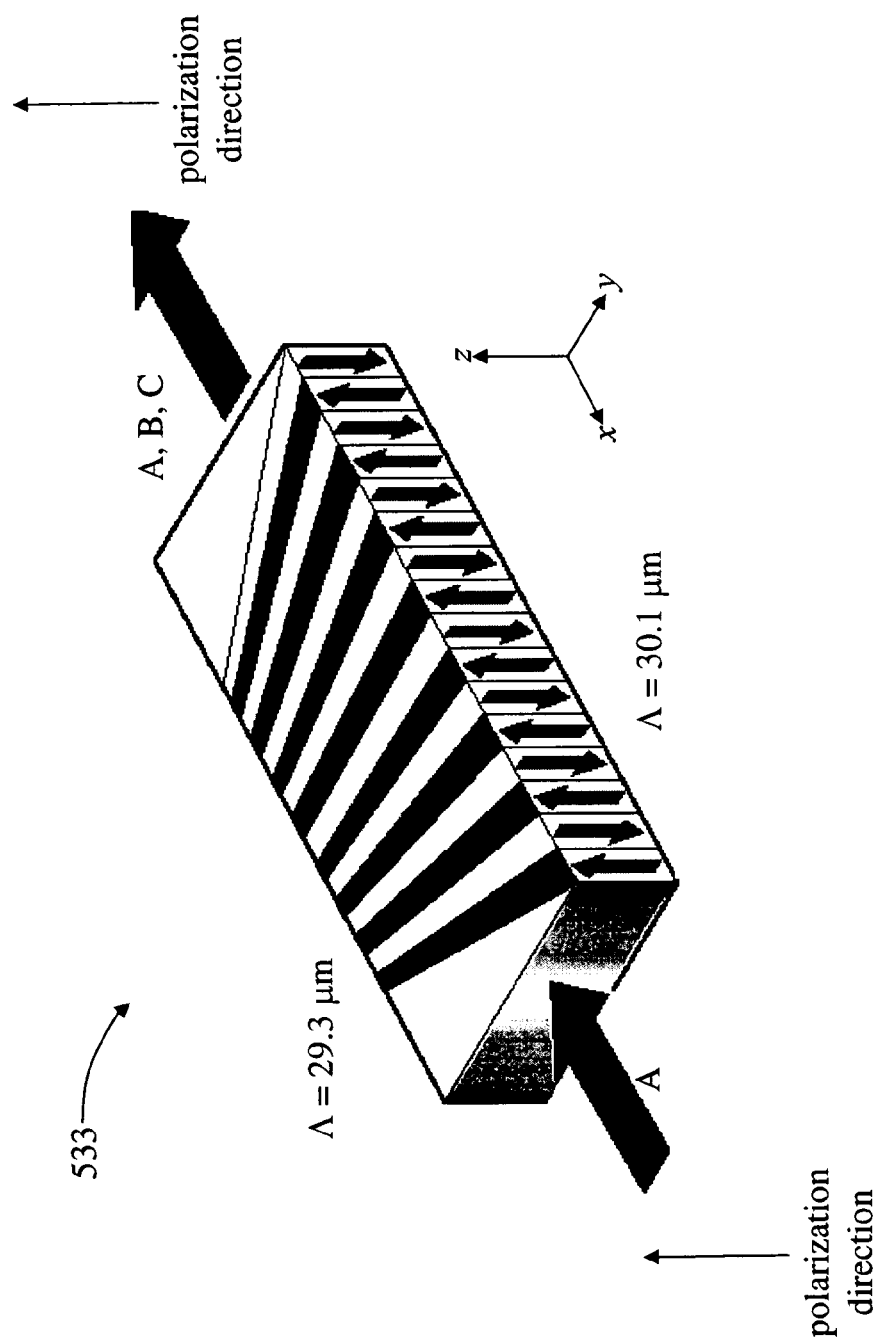
FIG. 5 is a perspective view of a periodically poled lithium niobate nonlinear material of the preferred embodiment.

FIG. 5 shows a preferred non-linear material 333 as a periodically poled lithium niobate (PPLN) crystal 533 that converts beam A into beams B and C. Beam A drives the non-linear material 333, and is usually called the "pump beam." The two output beams have different photon energies (wavelengths). Beam B has the lower photon energy (longer wavelength), and is commonly called the "idler beam," and beam C has the higher photon energy (shorter wavelength), and is commonly called the "signal beam." The wavelengths of the signal and idler beams are adjustable according to the nonlinearities of the non-linear material and the resonant modes of the cavity, as well as the wavelength of the pump beam. The energy of the generated beams B and C equals the energy of the converted portion of beam A, and the sum of the frequency of beams B and C equals the frequency of beam A.

PPLN crystal 533 is used to tunably convert light from beam A into beam B over a wavelength range that is useful for spectroscopic measurements of organic compounds. One embodiment PPLN crystal 553 is the fan-type crystal shown in FIG. 5, and described in U.S. Pat. No. 6,359,914 and incorporated herein by reference. The preferred embodiment PPLN crystal 533 has the following dimensions along the x, y, and z axis, respectfully: 50 mm long, 20 mm wide, and 0.5 mm thick. Crystal 533 has a 1° wedge between the input and output facets (the faces perpendicular to the x axis) to help eliminate idler feedback in OPO 330. The faces of PPLN crystal 533 have anti-reflection coatings at both 1.064 µm and at 1.57 µm. PPLN crystal 533 has a theoretical tuning range of about 350 cm$^{-1}$ at 180° C., and can convert pump beam A having a wavelength $\lambda_A$ of 1.06 µm into a signal beam (beam C) having a wavelength $\lambda_C$ that is adjustable from 1.53 to 1.62 µm and an idler beam (beam B) having a wavelength $\lambda_B$ that is related to wavelength $\lambda_B$ and is adjustable from 3.1 to 3.5 µm.

Figure 12:
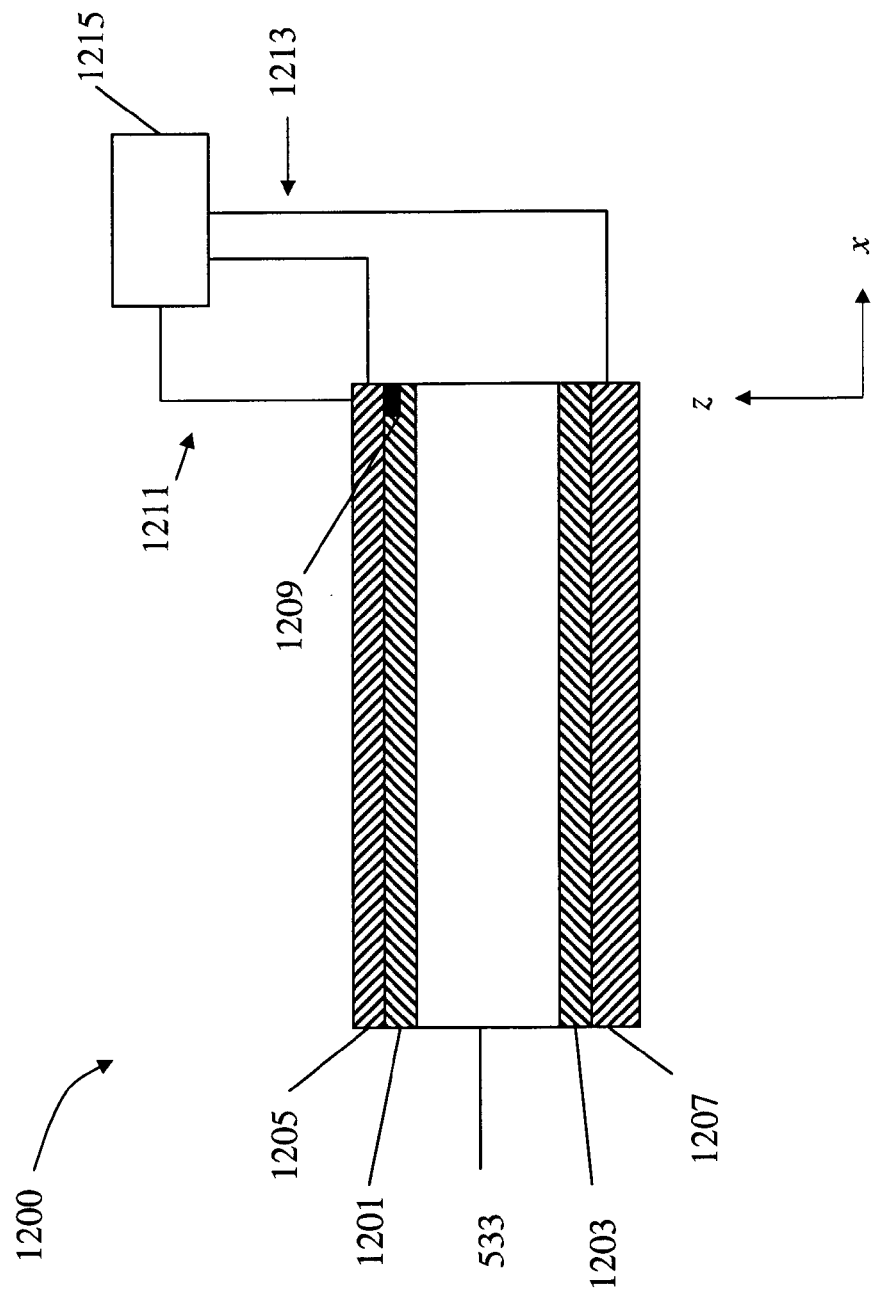
FIG. 12 is a side view of a PPLN crystal in an oven.

The temperature of PPLN crystal 533 is controlled as shown in FIG. 12, which shows the PPLN crystal in an oven 1200 having an upper portion 1201, an upper portion heater 1205, a lower portion 1203, and a lower portion heater 1207. The two planes of PPLN crystal 533 bound by surfaces parallel to the x-y plane, shown in FIG. 5, are in thermal contact with portions 1201 and 1203, respectively. Oven 1200 also includes a temperature sensor 1209 and a control system 1215. Control system 1215 receives oven temperature information from sensor 1209 through an electric connection 1211 and provides power to heaters 1205 and 1207 through connections 1213. It is preferred that portions 1201 and 1203 are highly thermally conductive materials, such as copper, and that heaters 1205 and 1207 are electric resistance heaters. Control system 1215 is instructed to maintain a prescribed temperature of crystal 533 and supplies power accordingly to heaters 1205 and 1207 to maintain this temperature. temperature. While it is preferred that control system 1215 is a stand-alone system with a non-changing prescribed temperature, control system 1215 is alternatively a controller programmed by 370.

The prescribed temperature must meet two requirements. First, the optical properties of PPLN crystal 533 are temperature dependent, with thermally-induced changes in the refractive index having a large impact on the wavelengths $\lambda_B$ and $\lambda_C$ To maintain control of the wavelengths of light generated by crystal 533 to the degree required for detailed spectroscopic analysis, the prescribed temperature should be maintained to within 0.01° C. Second, PPLN crystals are known to suffer from photorefractive damage. This damage is mitigated by heating the PPLN crystal 533 to a temperature high enough to allow the crystal to anneal. It is believed that a prescribed temperature of 180° C. is sufficient to anneal the crystal, though other temperatures may achieve the same effect. It is preferred that oven 1200 maintain the temperature of PPLN crystal 533 to 180.0±0.1° C.

Three axes of crystal 533 are shown in FIG. 5 as x, y, and z. The optical properties of crystal 533 are constant in the z direction, and are periodic for a beam propagating perpendicular to the z axis. Specifically, crystal 533 has periodic properties that depend on the y position, with periods that vary from Λ=29.3 to Λ=30.1 µm at increasing values of y. Incident beam A is thus subject to periodically changing optical properties as it propagates through crystal 533 in the x direction It is important that the polarization of beam A, as indicated in FIG. 5, is aligned in the z-direction to undergo conversion of similarly polarized beams B and C in crystal 533.

PPLN crystal 553, and in particular the period of the crystal, can be adjusted by moving the crystal along the y-axis and relative to pump beam A, producing non-linear interactions that generate two beams of different wavelengths that vary as a function of the position of the crystal along the y-axis. The use of a fan-type crystal for coarse tuning of OPO is described below.

While the previous description refers to pumping OPO 330 from laser system 320, the combined coarse and fine tuning capabilities of OPO 330 can produce tunable output using other pumping lasers or laser systems having sufficient output and at a proper wavelength to enable the OPO to generate beam B. Thus, for example, beam A of FIGS.

4A–4C can be a beam from a different light source with 1μ output having that is spectrally narrow and has an output in the watt range that is polarized as previously described with respect to the PPLN crystal.

Tuning the Optical Parametric Oscillator

Preferred OPO 330 combines coarse tuning and fine tuning to scan a large range of wavelength $\lambda_B$ with high resolution. Coarse and fine tuning are individually and collectively controlled by processor 373 to scan wavelength $\lambda_B$ through the combined commands of control signals controls $S_{\lambda\ coarse}$ and $S_{\lambda\ fine}$, respectively. One scanning technique is to repeatedly scan the fine tuning range while the coarse tuning range is increased stepwise at the beginning of each fine tuning range. The fine tuning can be either continuous or discrete depending on the technique used, as described below. Non-monotonic scanning can be corrected by sorting the spectra according to a measurement of wavelength $\lambda_B$.

In general, preferred coarse tuning for OPO 330 is accomplished through changes to the non-linear material 333 within the optical cavity in response to a control signal $S_{\lambda\ coarse}$. Preferred fine tuning alters the optical cavity of OPO 330 through one or both of the following techniques. The first alters the optical cavity in response to a control signal $S_{\lambda\ fine-1}$ by adjusting elements within the cavity (such as etalon 341), allowing the oscillations to jump from one mode to another. This results in discrete changes in the output wavelength during tuning and is termed "mode-hop" tuning. The second alters the optical cavity in response to a control signal $S_{\lambda\ fine-2}$ by increasing or decreasing the cavity length through the movement of mirror 343, allowing the oscillating frequency can adjust accordingly, and is termed "continuous" tuning. FIG. 4A shows OPO 330' with coarse tuning and two fine tuning mechanisms-mode hop tuning using etalon 341 and continuous tuning through the translation of mirror 343. FIG. 4B shows details of the fine tuning mechanism of OPO 330" using only mode hop fine tuning by etalon 341. FIG. 4C shows details of the fine tuning mechanism of OPO 330''' using only continuous fine tuning by translation of mirror 343. The coarse and fine tuning techniques are described subsequently.

Coarse tuning through the movement of crystal 533 is achieved as follows. As noted above, crystal 553 is aligned for propagation of pump beam A along the x-axis, with periods varying along the y-axis from $\Lambda=29.3$ to $\Lambda=30.1$ μm. PPLN crystal 553, and in particular the period of the crystal, can be adjusted by moving the crystal along the y-axis and relative to pump beam A, producing non-linear interactions that generate two beams of different wavelengths that vary as a function of the position of the crystal along the y-axis. Coarse tuning using the fan-shaped PPLN crystal 533 is accomplished by moving the crystal in the "y" direction shown in FIG. 5 by first translator 335 in response to control signal $S_{\lambda\ coarse}$. Translator 335 can be a stepper motor or any other mechanism for repeatably and controllably translating crystal 533. PPLN crystal 533 has a theoretical tuning range of about 350 cm$^{-1}$ at 180° C., and can convert pump beam A having a wavelength $\lambda_A$ of 1.06 μm into a signal beam (beam C) having a wavelength $\lambda_C$ that is adjustable from 1.53 to 1.62 μm and an idler beam (beam B) having a wavelength $\lambda_B$ that is related to wavelength $\lambda_B$ and is adjustable from 3.1 to 3.5 μm. Translating crystal 533 approximately 0.04 mm moves the OPO gain peak approximately 4 cm$^{-1}$.

In fine mode-hop tuning, an etalon 341 in the optical cavity alters the effective length of the optical of OPO 330 by adjusting the spacing of the etalon with a motor controlled by signal $S_{\lambda fine-1}$. Although the etalon may be continuously varied, the optical cavity of the OPO prefers to oscillate at discrete frequencies, and changes in etalon 341 result in discrete changes in the tuned frequency of the OPO. For the embodiment of FIGS. 4A and 4B, etalon 341 provides fine-frequency steps on the order of 0.6 to 1.2 GHz. The longitudinal mode spacing of OPO 330 is on the order of approximately 570 MHz, and thus the frequency changes during mode hoping correspond to 1 to 2 cavity modes. Uncontrollable perturbations of the OPO can result in mode hopping, and thus it can be difficult to achieve control of the mode hops to within a mode or two.

Since OPO 330 tends to oscillate in a single mode without intra-cavity elements, etalon 341 has to constrain only the oscillating mode, which allows the use of weakly frequency selective (or "low-finesse"), low-loss etalons. This is important since the OPO can only tolerate cavity losses on the order of 5% or less. Although fine tuning has been demonstrated in many laser systems, there are some subtle yet important differences in both OPO tuning and in the use of PPLN.

Figures 7A, 7B:
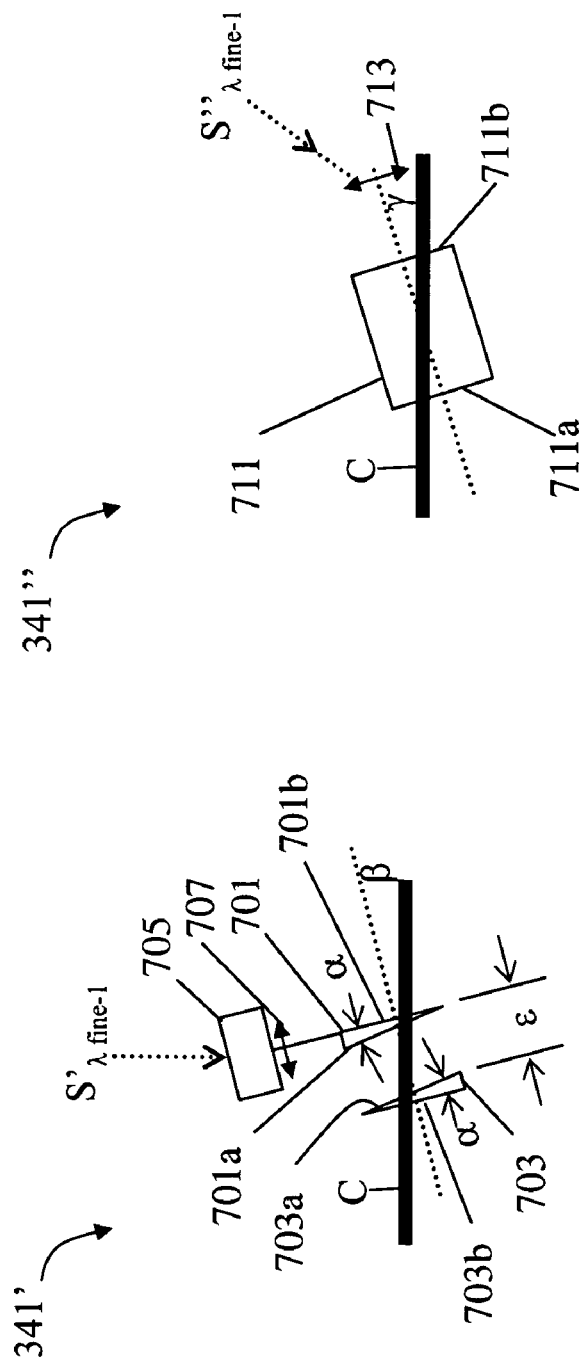
FIGS. 7A and 7B are schematic diagrams of an air-spaced etalon of the preferred embodiment and a solid rotating etalon of the preferred embodiment, respectively.

Several types of etalons 341 can be used as in inter-cavity etalon with an OPO as shown in FIGS. 4A and 4B, for example, the etalon can be either an air-spaced etalon 341', as shown in FIG. 7A, or a rotating solid etalon 341", as shown in FIG. 7B. It is important that the reflectivity or spectral rejection of the etalon be quite low—on the order of a few percent or so, since there is a tradeoff between reflectivity and required pump power.

Rotating solid etalon 341" includes a solid etalon material 711 and rotation stage (not shown) that rotates material 711 through an angle γ in the plane of FIG. 7B in response to control signal $S''_{\lambda\ fine-1}$, as indicated by arrow 713. Rotation through an angle γ of a few degrees with etalon 341 " in the path of beam C tunes OPO 330' or 330" over a few wavenumbers. A preferred rotating solid etalon 341" is a 400 μm thick, uncoated YAG substrate. Measurements using the Coherent light source with OPO 330 indicate that this etalon gives the best combination of mode hop step size, tuning range (several hundred wave numbers), and power (approximately 120 mW maximum in the idler), with a pump depletion typically in the range of 40–50% for 6 W of pump power. Although the rotation is nearly continuous, the frequency steps are discrete on the order of 0.02–0.1 cm$^{-1}$, depending on the number of cavity modes jumped. Various performance factors limit the solid etalon mode-hop tuning to the range of approximately 4 cm$^{-1}$.

Figure 9:
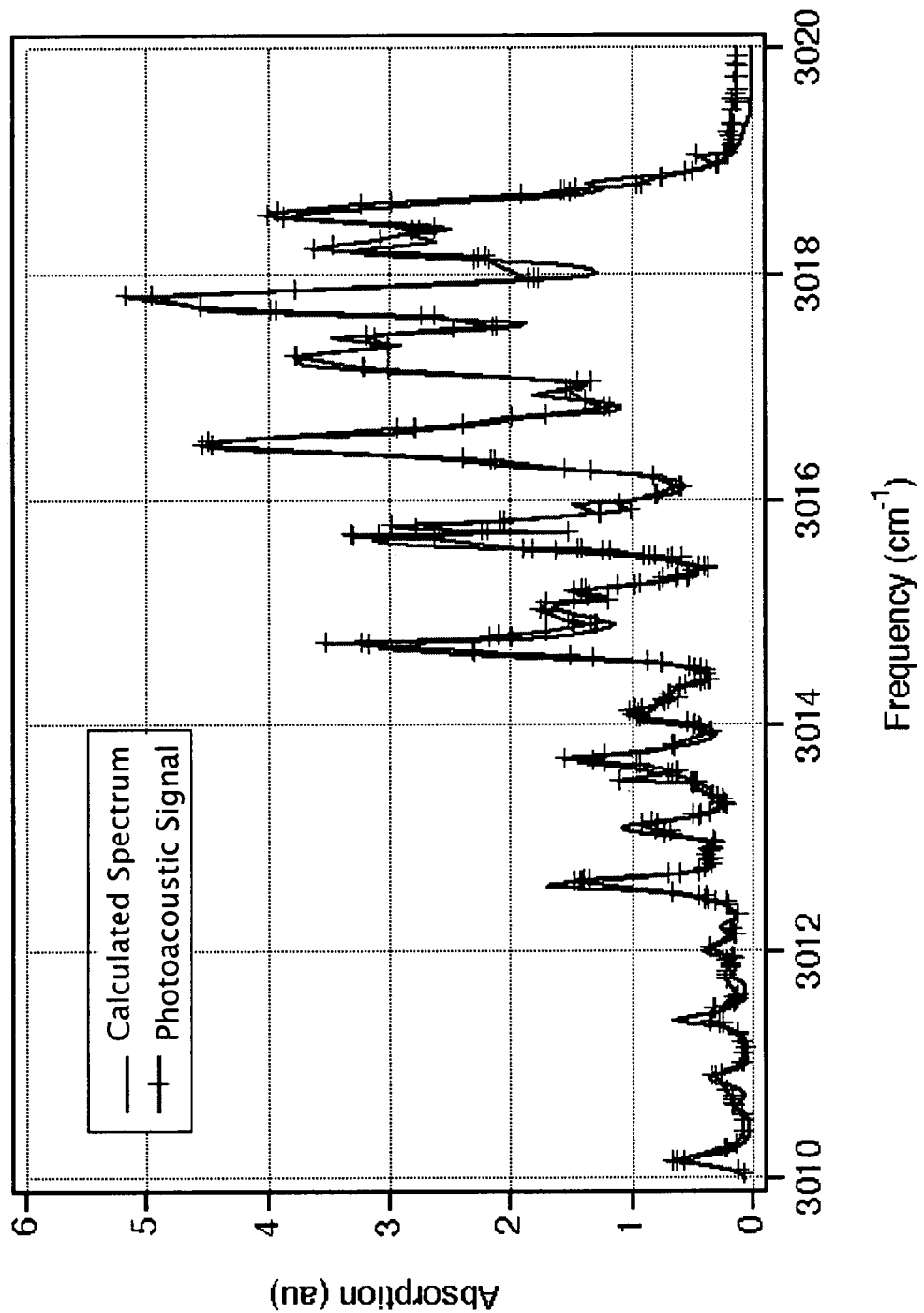
FIG. 9 is a graph of the photoacoustic spectrum of the methane Q branch as obtained with the preferred embodiment OPO pumped with the Coherent light source and the theoretical spectrum.

To illustrate the use of a mode-hop-tuned PPLN OPO in spectroscopic applications, FIG. 9 shows the photoacoustic spectrum of the methane Q branch as obtained with OPO 330 pumped with the Coherent light source, along with the theoretical spectrum. This spectrum was acquired at atmospheric pressure where pressure broadening is large. The scan of FIG. 9 was acquired by simultaneously tuning the PPLN crystal 533 combined with rotation of the solid etalon 341". Approximately four etalon scans were necessary to cover the 10 cm$^{-1}$ spanned by the methane Q branch, resulting in a broad and finely resolved spectrum.

There are several drawbacks however, of using a rotating solid etalon. First, the scan rate depends nonlinearly (quadratically) on etalon angle which requires software to linearize the scan and furthermore, the intra-cavity loss also depends nonlinearly with angle.

Air-spaced etalon 341' overcomes some of the problems encountered with solid etalons by having a constant tuning rate and a constant insertion loss which reduces the possibility of etalon mode hops. Air-spaced etalon 341' is shown in FIG. 7A includes of two wedged fused, UV-grade silica substrates, 701 and 703. Each substrate has a pair of sides that approximately perpendicular to beam C: a pair 701a and 701b, and 703a and 703b, respectively. Each pair of sides forms an angle, α, of approximately 30'. Substrates 701 and 703 are oriented with adjacent thick and thin portions, spaced apart by a distance ε of approximately 0.5 to 1.5 mm. One side of each substrate 701 and 703 has a 1.5 μm AR coating, and the other side of each substrate has no coating, yielding a reflectivity of approximately 5% and reducing misalignment. Air-spaced etalon 341 was inserted into OPO 330 at an angle, β, approximately 0.5° off of normal incidence of beam A to avoid optical feedback. A piezoelectric element 705 responds to control signal $S_{\lambda\ fine-1}$ to tune the distance between the substrates of the air-spaced etalon as indicated by arrow 707. Piezoelectric element 705 is preferably an annular element adapted to tune the etalon spacing over approximately 3 μm, resulting in a tuning range on the order of 10–50 cm$^{-1}$, depending on the etalon mirror spacing.

Figure 10:
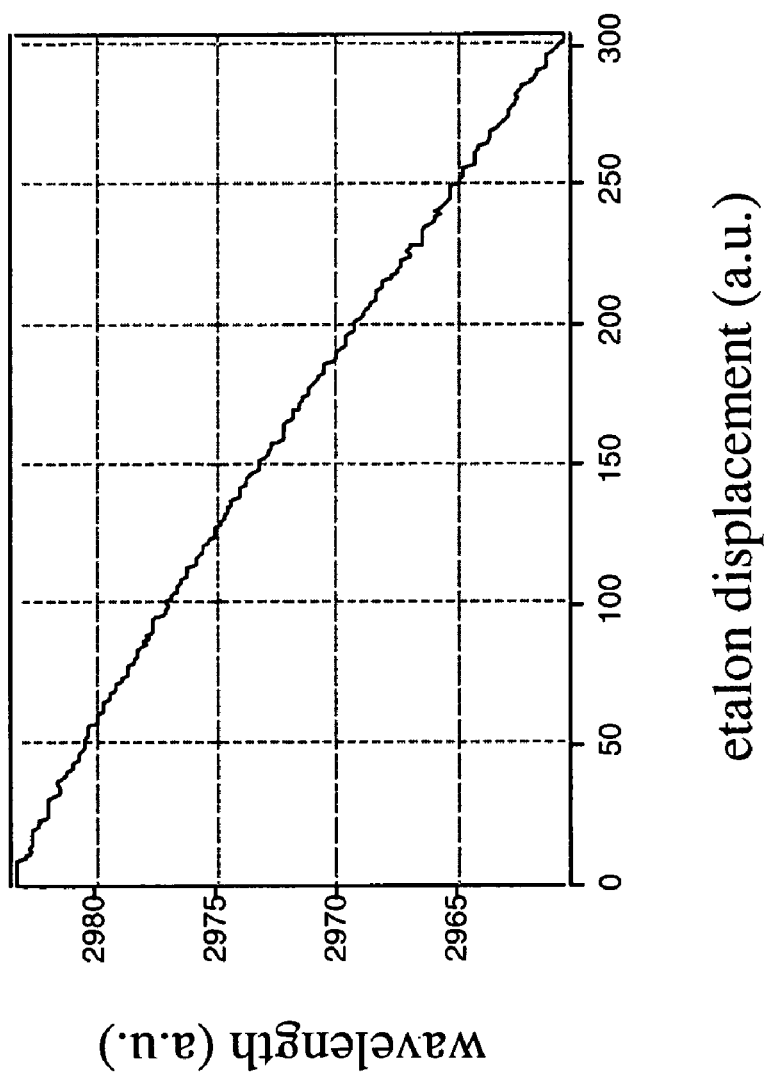
FIG. 10 is a graph showing the scanning characteristics of an air-spaced etalon as the output wavelength of beam as a function of the etalon displacement.

An example of a scan obtained with the air-spaced etalon is shown in FIG. 10, which shows, in arbitrary units, the output wavelength of beam D as a function of the etalon displacement, ε, and displays a mode-hop scan over 20 cm$^{-1}$ obtained with a scanning air-spaced etalon and synchronized with the tuning of crystal 533. For this scan, the etalon displacement is scanned by approximately 0.1 μm at an average spacing of 1.5 mm, yielding frequency steps on the order of 0.1 cm$^{-1}$. Scan non-linearities result, in part, from differential tuning between the etalon transmission peaks and the PPLN gain peak, and also by nonlinearities inherent in the piezo, especially at higher driving voltages. Also, while an air-spaced etalon has the advantage over the solid etalon of a constant insertion loss, the oscillation threshold is somewhat higher (approximately 4 W when pumped with the 6 W Nd:YAG laser), with a corresponding reduced output power (approximately 80 mW of idler power).

Since both the solid and air-spaced etalons used in OPO 330 are of low finesse, any secondary eltaoning or wavelength-dependent absorption or reflection can influence tuning. These effects include intra-cavity absorption by a gas, such as $CO_2$, etaloning in crystal 333, and mirror reflectivity at 3.3 μm. Thus for example, residual reflectivity of the cavity mirrors at 3.3 μm can cause OPO 330 to become doubly resonant, causing instabilities. Also, idler feedback as small as 10$^{-4}$ can affect stability. These effects can be eliminated through better multiband coatings on the flat cavity mirrors.

For continuous tuning, the cavity length of OPO 330' or OPO 330'" is adjusted by moving mirror 343 with second translator 345 in response to control signal $S_{\lambda\ fine-2}$. A reliable method of translation on this scale is through the use of piezo-electric transducers 345. The OPO cavity used a multiple stack piezo-electric transducer which was capable of translations on the order of 40 μm. The effective tuning is twice this since the optical cavity length changes by twice the translation amount. As the cavity length shortened, the cavity modes shift to shorter wavelengths. For OPO 330', etalon 341 is then controlled by a lock-loop to track the peak of a cavity mode as the cavity is tuned. Tuning is accomplished by keeping etalon 341 locked to the cavity mode as the cavity length is tuned.

There are many perturbations which can disrupt the tuning process, such as air currents inside the cavity caused by the PPLN oven since thermal changes in PPLN crystal 533 can change the effective optical length of the cavity. Some of the perturbations such as convection currents generated by the PPLN oven can be controlled by thermally isolating the oven. Other perturbations, like the rapid thermal fluctuations inside the PPLN crystal (caused in part by absorption of 3 μm light in the crystal) cannot be controlled. If the perturbations occur too rapidly, i.e., outside the bandwidth of the lock loop or if the perturbation was too large then the OPO may uncontrollably mode hop. To keep the insertion losses low the etalon was of relatively low-finesse making the cavity more susceptible to mode hops. The etalon also had to be of low mass so that the loop response frequency is high.

The application of the continuous tuning methods described herein to tunable OPOs presents many challenges. In particular, although mirror 337 and the mirrors in etalon 341 are designed to transmit at 3.3 μm, there is enough feedback to cause a double resonance effect. Doubly resonant OPOs are in general very unstable. As the cavity length defined by the path of beam C in OPO 330 is tuned, the 1.5 μm light of beam C tunes continuously, whereas the 3.3 μm light of beam B tunes continuously in the opposite direction. To complicate matters, there are occasions when the 3.3 μm light is slightly resonant in the cavity, which raises the intra-cavity 3 μm power. This in turn raises the temperature of crystal 333 which effectively changes the optical length and causes the laser to tune uncontrollably. To mitigate this problem, alternative OPOs have optical components that are more effective in rejecting intra-cavity 3.3 μm light.

Cell Calibration and Data Acquisition

To obtain an interpretable photoacoustic spectrum, it is preferable that the pressure signal, $S_P$, is normalized by intensity of the incident light, $S_I$, by dividing the pressure signal by the incident light signal. As noted above, one embodiment includes two separate lock-in amplifiers 371, one which accepts reference signal $S_{ref}$ and intensity signal $S_I$, and the other accepts reference signal $S_{ref}$ and pressure signal $S_P$. Since the pressure and intensity signals are modulated by a rate given by the reference signal, amplifier 371 can use $S_{ref}$ to obtain an accurate indication of the pressure and intensity. The ratio of the amplified pressure and intensity signals provides an intensity normalized spectral signal. Intensity normalization compensates for intensity fluctuations, but other effects such as detector nonlinearity, detector window etaloning, detector homogeneity, and beam profile changes all can cause residual noise. It has been determined that lens 314 helps to reduce some of these sources of error.

In general, the sampled gas will contain a mixture of gases having unknown concentration. Obtaining quantitative speciation of a spectrum requires that calibrated photoacoustic spectra be obtained for each species to be identified, preferably at more than one concentration. The following procedures were found to give acceptable results when using light from OPO 330 pumped with the Coherent light source. The cell responsively, R, is required to quantify the raw normalized pressure data. R has units, for example, of μ Volts/(C*mW*α), where α is the absorption (1/ppm-m) and C is the concentration in ppm. If the cell is operated at a pressure other than at atmospheric pressure, it is preferable that absolute concentration units. Gases with known absorptions (α's) and concentrations are used to determine the cell responsivity. Under atmospheric conditions the calibration should be independent of the calibration gas since energy transfer from vibration/rotation to translation (heat) is nearly 100%.

Calibration was obtained for several gases: methyl ethyl ketone, isopropyl acetate, n-butyl acetate and butane. Calibration constants varied from 103 (butane) to over 300 $\mu$V-m/mW. There were several reasons for the wide variations; some of the VOCs were slightly polar and therefore stuck to the surfaces of the gas bottle and photoacoustic cell, thus lowering the effective concentration, and second, the absorptions of some of the VOCs were not known accurately. For butane however, which is a nonpolar species, the calculated cell responsivity was from 150–200 $\mu$V-m/mW at high concentrations (>50 ppm) but at low concentrations (5 ppm) was reduced to approximately 80. The source of this discrepancy has not yet been determined but we have found variations as large as 20% in the gas dilution system. An adequate approximate calibration constant of 200 $\mu$V-m/mW was used in measurements using the Coherent light source for a two pass configuration.

Alternative Laser Embodiments

Figure 11:
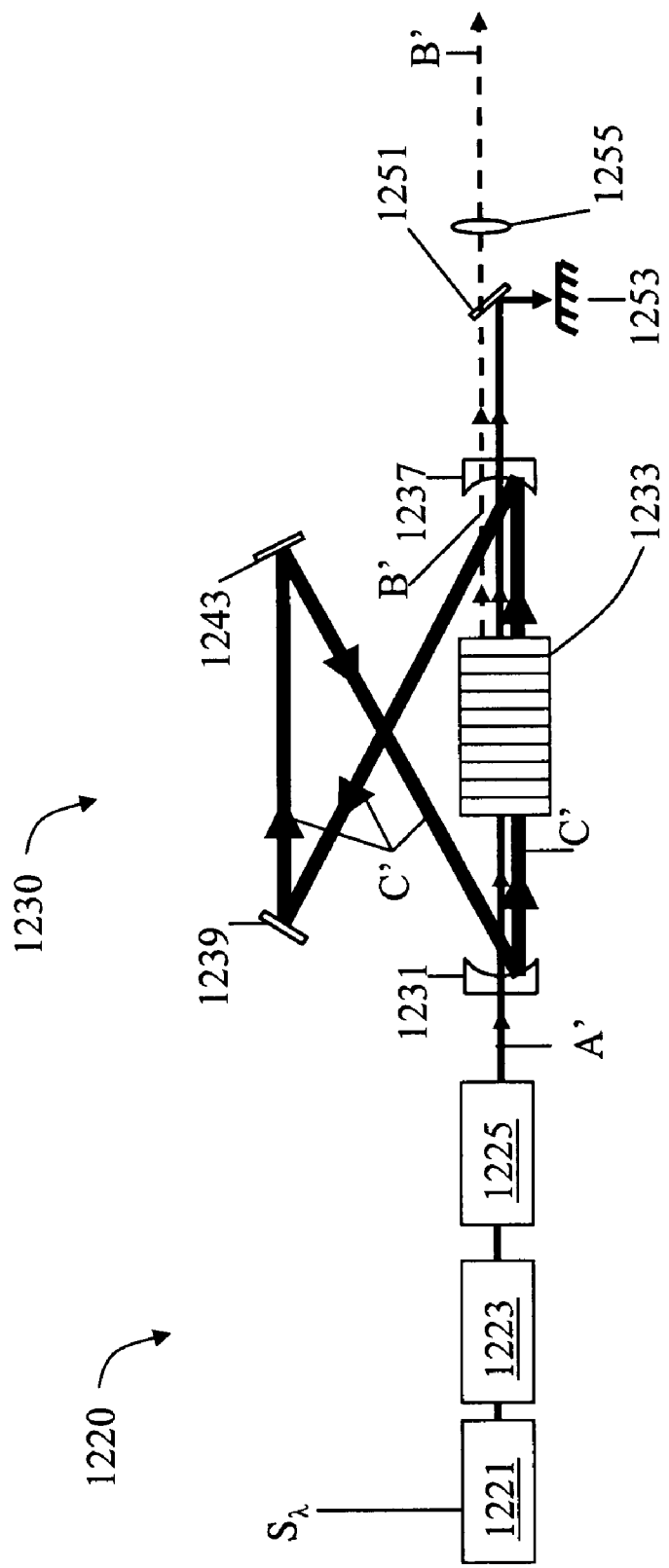
FIG. 11 is an alternative embodiment laser system and OPO.

An alternative embodiment laser system and OPO operating near 750 to near 900 nm is shown in FIG. 11. Specifically, FIG. 11 shows a laser source 1220 and an OPO 1230 that are alternatives to laser source 320 and OPO 330 of spectrometer 300. Laser source 1220 includes a diode seed laser 1221, a Faraday isolator 1223, and a tapered waveguide amplifier 1225. Laser source 1220 generates a beam A' that is controllable about a wavelength in the range of from 750 to 900 nm according to control signal $S_\lambda$. Lasers of this type include Ti:sapphire and diode lasers, and are generally tunable over a broad range, such as from 700 to 1000 mm, and can have a narrow band width of 1 MHz.

OPO 1230 includes a pair of plano-concave mirrors 1231 and 1237, a pair of planar mirrors 1239 and 1243, a non-linear optical material 1233, an etalon 1241 a beam splitter 1251, a beam dump 1253, and a lens 1255. Non-linear optical material 1233, which can be a PPLN crystal of constant poling frequency, is temperature controlled in a manner similar to crystal 533, generates a signal beam B' and an idler beam C'. OPO 1230 is singly resonant at the wavelength of signal beam B'. As the wavelength of beam A' is varied, the OPO resonates at a fixed signal wavelength and wavelength of idler beam C' varies according to changes in the pumping wavelength of beam A'. Etalon 1241 can be an air-spaced etalon, similar to etalon 341' or a solid etalon, similar to etalon 341", is used in OPO 1230 to hold the wavelength of signal beam B' fixed, allowing the wavelength of idler beam C' to follow the wavelength of pump beam A'. Mirrors 1231 and 1237 are coated on both sides for high transmission (>98%) of the pump beam A' and for high reflectivity (>99.5%) on the curved surfaces at the wavelength of signal beam B'.

These operating characteristics make laser 1221 are sufficient to provide sufficient range and controllability to speciate complex organic molecules. In addition, such lasers have greater efficiencies than longer wavelength lasers and can operate an OPO with less power, the total size and efficiency of a photoacoustic spectrometer system operating with a pump laser having a wavelength in the range from 750 to 900 m are reduced over those of a 1 $\mu$m laser. In addition, the laser is readily tunable, allowing for tuning of the OPO via changes in the pump wavelength. In such a system the OPO would be singly resonant at a fixed signal frequency and OPO output idler wavelength would follow changes in the pump wavelength. This would eliminate the need for intra-cavity tuning elements within the OPO.

The invention has now been explained with regard to specific embodiments. Variations on these embodiments and other embodiments may be apparent to those of skill in the art. It is therefore intended that the invention not be limited by the discussion of specific embodiments. It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A photoacoustic spectrometer for analyzing a sample comprising:
   a light source having a laser and an optical parametric oscillator (OPO) for generating a beam of an adjustable wavelength light from said laser,
   where said OPO has a light path, a first tuner including a material with non-linear optical properties within said light path, and a second tuner within said light path;
   a photoacoustic cell to contain the sample and having
     at least one window to accept said generated beam and irradiate a sample, and
     a pressure transducer adapted to provide an indication of the pressure of the sample; and
   a controller for adjusting said first tuner and said second tuner to scan said adjustable wavelength by mode hopping the oscillating frequency of said OPO.

2. The photoacoustic spectrometer of claim 1, wherein said material is a periodically polled lithium niobate (PPLN) crystal, wherein said light source includes an optical-fiber amplifier, and wherein said optical-fiber amplifier is an Ytterbium doped fiber.

3. The photoacoustic spectrometer of claim 2, further including a modulator in said beam to produce a periodic beam.

4. The photoacoustic spectrometer of claim 3, further comprising a light detector capable of determining an indication of the amplitude of said beam.

5. The photoacoustic spectrometer of claim 1, wherein said second tuner includes an air-spaced etalon.

6. The photoacoustic spectrometer of claim 5, wherein said first tuner is simultaneously adjusted with said second tuner.

7. The photoacoustic spectrometer of claim 1, further including a modulator in said beam to produce a periodic beam, a light detector capable of determining an indication of the amplitude of said beam, and a lock-in amplifier to receive the output of said pressure transducer and said light detector and generate a signal indicative of the pressure induced in the sample by the periodic beam.

8. The photoacoustic spectrometer of claim 7, wherein said controller scans said adjustable wavelength, and wherein said generated lock-in amplifier signal produces an indication of the pressure induced by the sample during the scanning of said adjustable wavelength.

9. The photoacoustic spectrometer of claim 1, where said at least one window includes at least one window to permit accepted light to pass from said photoacoustic cell, and further including a reflective surface to accept light passing from said photoacoustic cell and reflect said light back through said photoacoustic cell.

10. The photoacoustic spectrometer of claim 1, wherein said adjustable wavelength light is adjusted by adjusting the wavelength of the laser light and by adjustments to said first or second tuners.

11. The photoacoustic spectrometer of claim 1, further including one or more batteries, wherein the power to operate photoacoustic spectrometer is provided by said one or more batteries.

12. A photoacoustic spectrometer for analyzing a sample comprising:
- a light source having a laser system including a laser and an optical-fiber amplifier adapted to amplify light from said laser, and an optical parametric oscillator (OPO) for generating a beam of an adjustable wavelength light from said amplified laser, where said OPO has a light path and a material with non-linear optical properties and an air-spaced etalon within said light path for tuning said adjustable wavelength;
- a photoacoustic cell to contain the sample and having
  - at least one window to accept said generated beam and irradiate a sample, and
  - a pressure transducer adapted to provide an indication of the pressure of the sample; and
- a controller to scan said adjustable wavelength.

13. The photoacoustic spectrometer of claim 12, wherein said non-linear optical material is a periodically polled lithium niobate (PPLN) crystal and wherein said optical-fiber amplifier is an Ytterbium doped fiber.

14. The photoacoustic spectrometer of claim 13, further including a modulator in said beam to produce a periodic beam.

15. The photoacoustic spectrometer of claim 14, further comprising a light detector capable of determining an indication of the amplitude of said beam.

16. The photoacoustic spectrometer of claim 13, wherein said material and said air-spaced etalon are moved simultaneously to fine tune of said adjustable wavelength.

17. The photoacoustic spectrometer of claim 16, wherein said air-spaced etalon changes the adjustable wavelength by mode-hopping.

18. The photoacoustic spectrometer of claim 16, further including a modulator in said beam to produce a periodic beam, a light detector capable of determining an indication of the amplitude of said beam, and a lock-in amplifier to receive the output of said pressure transducer and said light detector and generate a signal indicative of the pressure induced in the sample by the periodic beam.

19. The photoacoustic spectrometer of claim 18, wherein said controller scans said adjustable wavelength, and wherein said generated lock-in amplifier signal produces an indication of the pressure induced by the sample during the scanning of said adjustable wavelength.

20. The photoacoustic spectrometer of claim 12, wherein said at least one window includes at least one window to permit accepted light to pass from said photoacoustic cell, and further including a reflective surface to accept light passing from said photoacoustic cell and reflect said light back through said photoacoustic cell.

21. The photoacoustic spectrometer of claim 16, wherein said adjustable wavelength light is adjusted by adjusting the wavelength of the laser light and by adjustments to said material or said air-spaced etalon.

22. The photoacoustic spectrometer of claim 19, further including one or more batteries, wherein the power to operate photoacoustic spectrometer is provided by said one or more batteries.

23. A photoacoustic spectrometer for analyzing a sample comprising:
- a light source having a laser system including a laser having an output with an adjustable wavelength of approximately 750 to approximately 900 nm and a tapered waveguide amplifier adapted to amplify light from said laser, and an optical parametric oscillator (OPO) for generating a beam of an adjustable wavelength light from said amplified laser, where said OPO has a fixed light path and a fixed non-linear material with non-linear optical properties within said light path;
- a photoacoustic cell to contain the sample and having
  - at least one window to accept said generated beam and irradiate a sample, and
  - a pressure transducer adapted to provide an indication of the pressure of the sample; and
- a controller to scan said adjustable wavelength.

24. The photoacoustic spectrometer of claim 23, wherein said non-linear optical material is a periodically polled lithium niobate (PPLN) crystal.

25. The photoacoustic spectrometer of claim 23, further including a modulator in said beam to produce a periodic beam.

26. The photoacoustic spectrometer of claim 25, further comprising a light detector capable of determining an indication of the amplitude, of said beam.

27. The photoacoustic spectrometer of claim 26, further including a lock-in amplifier to receive the output of said pressure transducer and said light detector and generate a signal indicative of the pressure induced in the sample by the periodic beam.

28. The photoacoustic spectrometer of claim 27, wherein said controller scans said adjustable wavelength, and wherein said generated lock-in amplifier signal produces an indication of the pressure induced by the sample during the scanning of said adjustable wavelength.

29. The photoacoustic spectrometer of claim 23, wherein said at least one window includes at least one window to permit accepted light to pass from said photoacoustic cell, and further including a reflective surface to accept light passing from said photoacoustic cell and reflect said light back through said photoacoustic cell.

* * * * *